US012781273B2

(12) United States Patent
Haselton et al.

(10) Patent No.: US 12,781,273 B2
(45) Date of Patent: Nov. 3, 2026

(54) PCR DETECTION OF SMALL FRAGMENTS OF A KNOWN NUCLEIC ACID TARGET

(71) Applicant: Vanderbilt University, Nashville, TN (US)

(72) Inventors: Frederick R. Haselton, Nashville, TN (US); Emily C. Kight, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 443 days.

(21) Appl. No.: 18/364,809

(22) Filed: Aug. 3, 2023

(65) Prior Publication Data

US 2024/0084372 A1 Mar. 14, 2024

Related U.S. Application Data

(60) Provisional application No. 63/394,834, filed on Aug. 3, 2022.

(51) Int. Cl.
*C12P 19/34* (2006.01)
*C12Q 1/686* (2018.01)

(52) U.S. Cl.
CPC .................................... *C12Q 1/686* (2013.01)

(58) Field of Classification Search
CPC ...................................................... C12Q 1/686
See application file for complete search history.

(56) References Cited

U.S. PATENT DOCUMENTS

2007/0077582 A1* 4/2007 Slepnev ............... C12Q 1/6886 435/6.16
2009/0023151 A1* 1/2009 Dawson ............... C12Q 1/6813 435/6.16
2017/0166954 A1* 6/2017 Vinayagamoorthy ....................... C12Q 1/6853

OTHER PUBLICATIONS

Bordelon, Hali, et al. "Design and use of mouse control DNA for DNA biomarker extraction and PCR detection from urine: Application for transrenal *Mycobacterium tuberculosis* DNA detection." *Journal of microbiological methods* 136 (2017): 65-70.
Markus, Havell, et al. "Sub-nucleosomal organization in urine cell-free DNA." *BioRxiv* (2019): 696633.
Nadano, Daita, Toshihiro Yasuda, and Koichiro Kishi. "Measurement of deoxyribonuclease I activity in human tissues and body fluids by a single radial enzyme-diffusion method." *Clinical chemistry* 39.3 (1993): 448-452.
Oreskovic, Amy, and Barry R. Lutz. "Ultrasensitive hybridization capture: reliable detection of< 1 copy/mL short cell-free DNA from large-volume urine samples." *PLoS One* 16.2 (2021): e0247851.

(Continued)

*Primary Examiner* — Kenneth R Horlick
(74) *Attorney, Agent, or Firm* — pH IP Law

(57) ABSTRACT

The present disclosure is directed to methods of detecting small fragments of known nucleic acid biomarkers. The method permits small fragment detection using a method that reconstructs a full-length amplicon from DNA fragments. The method includes use of a capture template oligonucleotide that contains part of a known biomarker amplicon sequence. When DNA amplicon fragments bind to this extension oligonucleotide, target fragments are elongated, and a full-length amplicon containing both primer sites is created, which is subsequently amplified by traditional method.

18 Claims, 13 Drawing Sheets

Specification includes a Sequence Listing.

(56) References Cited

OTHER PUBLICATIONS

Oreskovic, Amy, et al. "Characterizing the molecular composition and diagnostic potential of *Mycobacterium tuberculosis* urinary cell-free DNA using next-generation sequencing." *International Journal of Infectious Diseases* 112 (2021): 330-337.
Oreskovic, Amy, et al. "Diagnosing pulmonary tuberculosis by using sequence-specific purification of urine cell-free DNA." *Journal of clinical microbiology* 59.8 (2021): 10-1128.
Su, Ying-Hsiu, et al. "Transrenal DNA as a diagnostic tool: important technical notes." *Annals of the New York Academy of Sciences* 1022.1 (2004): 81-89.
Tsui, Nancy BY, et al. "High resolution size analysis of fetal DNA in the urine of pregnant women by paired-end massively parallel sequencing." *PloS one* 7.10 (2012): e48319.
Umansky, Samuil R., and L. David Tomei. "Transrenal DNA testing: progress and perspectives." *Expert review of molecular diagnostics* 6.2 (2006): 153-163.

* cited by examiner

SEQUENCE LISTING

```
Sequence total quantity: 7
SEQ ID NO: 1            moltype = DNA  length = 34
FEATURE                 Location/Qualifiers
source                  1..34
                        mol_type = other DNA
                        organism = synthetic construct
modified_base           1..34
                        mod_base = OTHER
                        note = r is ribouridine
SEQUENCE: 1
rrcgccracg rggccrrrgr caccgacgcc tacg                              34

SEQ ID NO: 2            moltype = RNA  length = 37
FEATURE                 Location/Qualifiers
source                  1..37
                        mol_type = other RNA
                        organism = synthetic construct
SEQUENCE: 2
ttcgcctacg tggcctttgt caccgacgcc tacgacg                           37

SEQ ID NO: 3            moltype = DNA  length = 37
FEATURE                 Location/Qualifiers
source                  1..37
                        mol_type = other DNA
                        organism = synthetic construct
modified_base           1..20
                        mod_base = OTHER
                        note = t is deoxyuridine
SEQUENCE: 3
ttcgcctacg tggcctttgt caccgacgcc tacgacg                           37

SEQ ID NO: 4            moltype = DNA  length = 42
FEATURE                 Location/Qualifiers
source                  1..42
                        mol_type = other DNA
                        organism = synthetic construct
modified_base           1..42
                        mod_base = OTHER
                        note = t is uracil
SEQUENCE: 4
ttcgcctacg tggcctttgt caccgacgcc tacgctcgca gg                     42

SEQ ID NO: 5            moltype = DNA  length = 42
FEATURE                 Location/Qualifiers
source                  1..42
                        mol_type = other DNA
                        organism = synthetic construct
modified_base           1..42
                        mod_base = OTHER
                        note = t is deoxyuridine
SEQUENCE: 5
ttcgcctacg tggcctttgt caccgacgcc tacgctcgca gg                     42

SEQ ID NO: 6            moltype = DNA  length = 90
FEATURE                 Location/Qualifiers
source                  1..90
                        mol_type = other DNA
                        organism = synthetic construct
SEQUENCE: 6
ttcgcctacg tggcctttgt caccgacgcc tacgacgctc gcaggttcgc ctacgtggcc  60
tttgtcaccg acgcctacga cgctcgcagg                                   90

SEQ ID NO: 7            moltype = DNA  length = 89
FEATURE                 Location/Qualifiers
source                  1..89
                        mol_type = other DNA
                        organism = synthetic construct
modified_base           1..22
                        mod_base = OTHER
                        note = t is deoxyuridine
modified_base           1..89
                        mod_base = OTHER
                        note = r is ribouridine
SEQUENCE: 7
ttcgcctacg rggccrrgtc accgacgcct acgacgctcg caggttcgcc tacgtggcct  60
ttgtcaccga cgcctacgac gctcgcagg                                    89
```

PCR DETECTION OF SMALL FRAGMENTS OF A KNOWN NUCLEIC ACID TARGET

STATEMENT REGARDING FEDERALLY SPONSORED RESEARCH

This invention was made with government support under grant no. R21AI152497 awarded by the National Institutes of Health. The government has certain rights in the invention.

REFERENCE TO A SEQUENCE LISTING

This application contains a Sequence Listing XML, which has been submitted electronically and is hereby incorporated by reference in its entirety. Said XML Sequence Listing, created on Aug. 2, 2023, is named VBLTP0330US.xml and is 10,685 bytes in size.

PRIORITY CLAIM

This application claims benefit of priority to U.S. Provisional Application Ser. No. 63/394,834, filed Aug. 3, 2022, the entire contents of which are hereby incorporated by reference.

BACKGROUND

1. Field of the Disclosure

The present disclosure relates generally to the fields of molecular biology, nucleic acid chemistry and methods of detecting small nucleic acid fragments.

2. Background

Short RNA and DNA fragments are of increasing interest as biomarkers of nucleic acid processing and regulatory function, and the presence of infectious agents. A particularly useful application of biomarkers is in using urine as a patient sample for detection of fragments of a known biomarker sequence. A problem unique to this type of patient sample is the presence of DNases which degrade the DNA and RNA present in the sample into small fragments. Many of these fragments are thought to be too short (<40 base pairs) to be detectable by traditional PCR or RT-PCR. The reason they are undetectable is that the fragments present do not contain both primer regions and therefore the PCR primers cannot bind on both the upstream and downstream side of the amplicon region to produce the usual exponential growth required for sensitive detection.

SUMMARY

In accordance with the present disclosure, there is provided a method of amplifying a fragment of a nucleic acid target in a sample comprising:

(a) adding to said sample (i) a nucleic acid template that partially hybridizes to and serves as an amplification template for a fragment of a nucleic acid target, (ii) a first polymerase capable of extending the fragment once hybridized to said nucleic acid template, and (iii) a nucleotide tri-phosphate mixture, wherein adding is under conditions supporting extension of the fragment once hybridized to said acid template;

(b) removing, degrading or masking the nucleic acid template from the product generated in step (a); and (c) contacting the product of step (b) with (i) a second polymerase, (ii) a nucleotide triphosphate mixture, and (iii) a forward primer, a under conditions supporting polymerization of a nucleic acid strand complementary to the extended fragment, wherein the nucleic acid template comprises a detection sequence and a capture sequence, wherein the detection sequence is 5' to the nucleic acid template, and wherein the first primer corresponds to a portion of the detection sequence. The nucleic acid template may comprise a detection sequence and a capture sequence, wherein said detection sequence is 5' to said capture sequence.

The method may further comprise adding a reverse primer after step (b), the reverse primer being (a) complementary to the extended fragment and located 3' to the region corresponding to the forward primer; and (b) present at a sufficiently low concentration to effect only linear amplification by polymerase chain reaction of the extended fragment. The method may further comprise adding additional reverse primer, thereby resulting in exponential amplification by polymerase chain reaction and subsequent detection of the extended fragment. The method may further comprise hybridizing the amplified extended fragment to a probe corresponding to or complementary to the detection sequence.

The first polymerase and second polymerase may be the same or different, such as where the first polymerase is a U-tolerant DNA polymerase or is a heat sensitive polymerase. The nucleic acid template may comprises RNA or DNA uracil bases, the first polymerase may be a U-tolerant DNA polymerase, and the method may comprise degrading RNA or DNA uracil bases in the nucleic acid template after step (a). The nucleic acid template may comprise RNA or DNA uracil bases, the first polymerase may be a U-tolerant DNA polymerase, and the method may comprise removing or inactivating the U-tolerant DNA polymerase after step (a) and replacing it with a U-intolerant DNA polymerase. The nucleic acid template may comprise RNA or DNA uracil bases, the first polymerase may be a heat sensitive RNA polymerase and the method may further comprise heat inactivating the heat-sensitive RNA polymerase after step (a).

The sample may have been treated prior step (a) to increase the concentration of the fragment, such as where the sample has been treated after step (a) to increase the concentration of the extended fragment and/or to remove the nucleic acid template. The nucleic acid template may be coupled to a lipid moiety or a bead, such as a magnetic bead or a glass bead. The method may further comprise removing the bead coupled nucleic acid template from the preparation of step (a), thereby leaving the extended fragment in solution. The bead may be a magnetic bead and removing comprises capturing the magnetic bead on a magnetized substrate, such as steel wool. The method may further comprise degrading any remaining nucleic acid template. The The nucleic acid template may be about 15 to about 2500 nucleotides in length. The partial nucleic acid target may be a deoxyribonucleic acid (DNA) and the first polymerase is a DNA polymerase, such as from *Mycobacterium tuberculosis*. The fragment may be a ribonucleic acid (RNA) and the first polymerase is an RNA polymerase, such as a reverse transcriptase. The sample may be urine.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DESCRIPTION OF ILLUSTRATIVE EMBODIMENTS

Figure 1A:
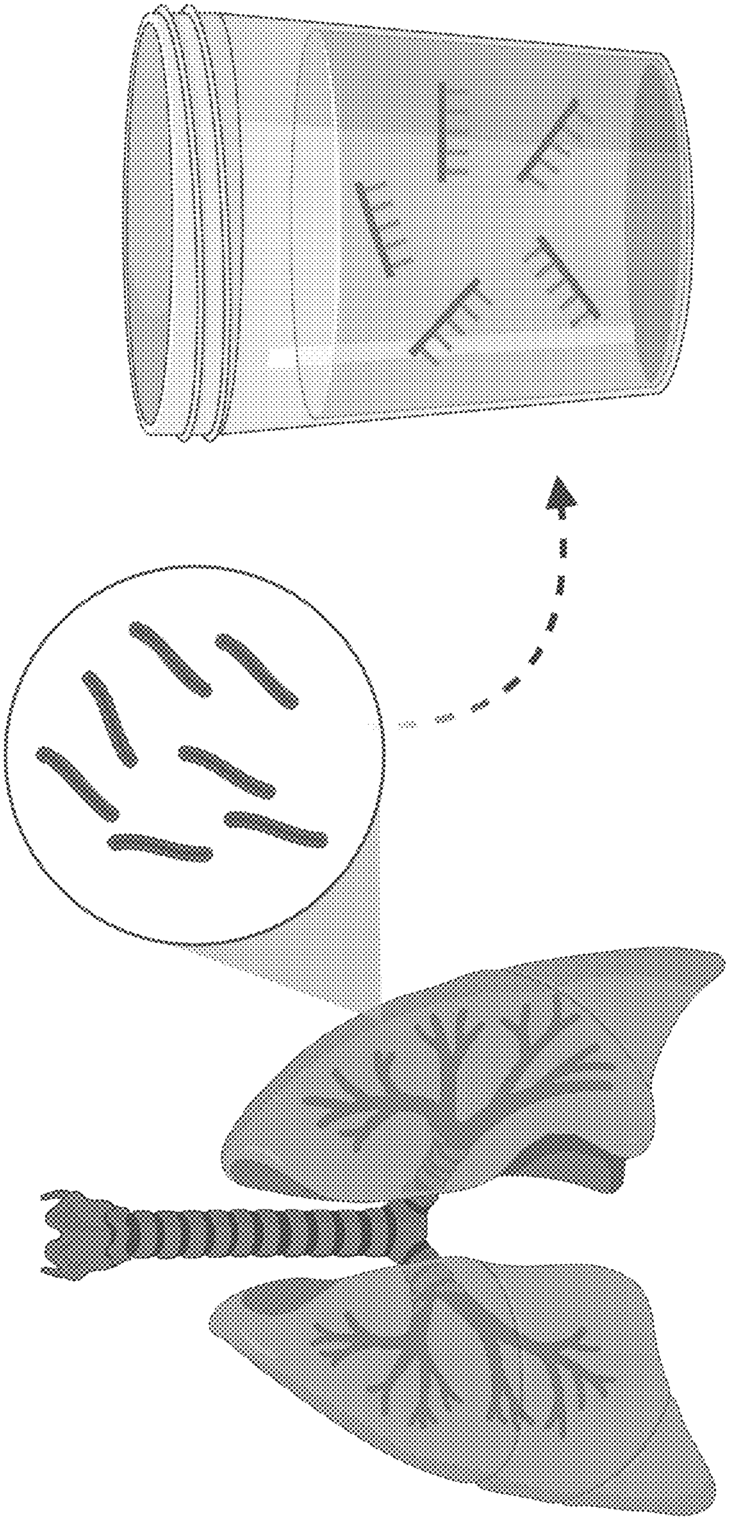
FIG. 1A Schematic of the overall processing of tuberculosis biomarkers and their transport to urine.

As explained above, biomarkers found in urine and potentially valuable in detecting and monitoring disease are notoriously difficult to detect. Here, the inventors have developed a small fragment detection method which reconstructs a full-length amplicon from DNA fragments. The method is based on including a capture template oligonucleotide that contains part of a known TB biomarker amplicon sequence. When DNA amplicon fragments bind to this extension oligonucleotide, target fragments are elongated, and a full-length amplicon containing both primer sites is created, which is subsequently amplified by traditional PCR. They refer to this process as amplicon reconstruction PCR and abbreviated AR-PCR.

A particular interest for the inventors is in the diagnosis of tuberculosis (TB). Most often this is achieved using a sputum sample. Many patients are not able to produce sputum (e.g., children) but non-invasive collection of urine is readily achievable. Several studies have shown that urine contains fragments of DNA and RNA that have passed from the blood into urine which some have begun to detect and characterize by using sequencing technologies. Unfortunately, sequencing is not available in many locations where the initial diagnosis and subtyping of the bacterial species is needed most. Moreover, PCR will not amplify a DNA sequence if it does not contain both of the primers. In some cases, fragmented DNA from the original full-length target may be present but are partially degraded by other biological processes. These will not be detected by PCR. Until recently the existence of tuberculosis (TB) DNA fragments in urine was controversial but recent publications suggest that they are present and detectable if the urine sample is treated to block degradation (36-38).

Here, the inventors describe an alternative PCR methodology, exemplified using TB, that can be used to detect nucleic acid fragments when a known target sequence is present. A key element here is the addition of sequences that are complementary to the fragments of the target amplicon that are extended by the PCR polymerase during the course of a normal PCR heat/cool cycle to extend the fragmented double-stranded DNA so that the reaction now contains full-length PCR amplicons that can be amplified subsequently. Using this method, the prevention of degradation may not be necessary and, in fact, may boost the sensitivity of this approach.

In addition to TB testing in urine, this technology can also be used to detect any known biomarker that has been partially degraded through RNase or DNase activity. This includes, for example, detection of a biomarker circulating in the blood that is associated with particular cancer. Some have been identified, but as more become known the method proposed here could serve as the detection platform. This approach not only takes advantage of the high sensitivity and specificity inherent in the PCR methodology but also the widespread availability of PCR instrumentation already in use in many settings for other diagnostic procedures.

These and other aspects of the disclosure are set out in detail below.

I. DEFINITIONS

"Amplification," as used herein, refers to any in vitro process for increasing the number of copies of a nucleotide sequence or sequences. Nucleic acid amplification results in the incorporation of nucleotides into DNA or RNA. As used herein, one amplification reaction may consist of many rounds of DNA replication. For example, one PCR reaction may consist of 2-100 "cycles" of denaturation and replication.

"Polymerase chain reaction," or "PCR," means a reaction for the amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. In some cases, the annealing and extension steps may be combined into a single step. Particular temperatures, durations at each step, and rates of change between steps depend on many factors well-known to those of ordinary skill in the art, e.g., exemplified by the references: McPherson et al., editors, PCR: A Practical Approach and PCR2: A Practical Approach (IRL Press, Oxford, 1991 and 1995, respectively).

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with its use in synthesis of primer extension products, and are usually are in the range of between 6 to 100 nucleotides in length, such as 6 to 70, 10 to 50, 10 to 75, 15 to 60, 15 to 40, 15 to 45, 18 to 30, 18 to 40, 20 to 30, 20 to 40, 21 to 25, 21 to 50, 22 to 45, 25 to 40, and any length between the stated ranges. In some embodiments, the primers are usually not more than about 6, 7, 8, 9, 10, 12, 15, 20, 21, 22, 23, 24, 25, 26, 27, 28, 29, 30, 35, 40, 45, 50, 55, 60, 65, or 70 nucleotides in length.

"Incorporating," as used herein, means becoming part of a nucleic acid polymer.

A "nucleoside" is a base-sugar combination, i.e., a nucleotide lacking a phosphate. It is recognized in the art that there is a certain inter-changeability in usage of the terms nucleoside and nucleotide. For example, the nucleotide deoxyuridine triphosphate, dUTP, is a deoxyribonucleoside triphosphate. After incorporation into DNA, it serves as a DNA monomer, formally being deoxyuridylate, i.e., dUMP or deoxyuridine monophosphate. One may say that one incorporates dUTP into DNA even though there is no dUTP moiety in the resultant DNA. Similarly, one may say that one incorporates deoxyuridine into DNA even though that is only a part of the substrate molecule.

"Nucleotide," as used herein, is a term of art that refers to a base-sugar-phosphate combination. Nucleotides are the monomeric units of nucleic acid polymers, i.e., of DNA and RNA. The term includes ribonucleotide triphosphates, such as rATP, rCTP, rGTP, or rUTP, and deoxyribonucleotide triphosphates, such as dATP, dCTP, dUTP, dGTP, or dTTP.

The term "nucleic acid" or "polynucleotide" will generally refer to at least one molecule or strand of DNA, RNA, DNA-RNA chimera or a derivative or analog thereof, comprising at least one nucleobase, such as, for example, a naturally occurring purine or pyrimidine base found in DNA (e.g., adenine "A," guanine "G," thymine "T" and cytosine "C") or RNA (e.g. A, G, uracil "U" and C). The term "nucleic acid" encompasses the terms "oligonucleotide" and "polynucleotide." "Oligonucleotide," as used herein, refers collectively and interchangeably to two terms of art, "oligonucleotide" and "polynucleotide." Note that although oligonucleotide and polynucleotide are distinct terms of art, there is no exact dividing line between them and they are used interchangeably herein. The term "adapter" may also be used interchangeably with the terms "oligonucleotide" and "polynucleotide." In addition, the term "adapter" can indicate a linear adapter (either single stranded or double stranded) or a stem-loop adapter. These definitions generally refer to at least one single-stranded molecule, but in specific embodiments will also encompass at least one additional strand that is partially, substantially, or fully complementary to at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss," a double-stranded nucleic acid by the prefix "ds," and a triple stranded nucleic acid by the prefix "ts."

A "nucleic acid molecule" refers to any single-stranded or double-stranded nucleic acid molecule including standard canonical bases, hypermodified bases, non-natural bases, or any combination of the bases thereof. For example, and without limitation, the nucleic acid molecule contains the four canonical DNA bases—adenine, cytosine, guanine, and thymine, and/or the four canonical RNA bases—adenine, cytosine, guanine, and uracil. Uracil can be substituted for thymine when the nucleoside contains a 2'-deoxyribose group. The nucleic acid molecule can be transformed from RNA into DNA and from DNA into RNA. For example, and without limitation, mRNA can be created into complementary DNA (cDNA) using reverse transcriptase and DNA can be created into RNA using RNA polymerase. A nucleic acid molecule can be of biological or synthetic origin. Examples of nucleic acid molecules include genomic DNA, cDNA, RNA, a DNA/RNA hybrid, amplified DNA, a pre-existing nucleic acid library, etc. A nucleic acid may be obtained from a human sample, such as blood, serum, plasma, cerebrospinal fluid, cheek scrapings, biopsy, semen, urine, feces, saliva, sweat, etc. A nucleic acid molecule may be subjected to various treatments, such as repair treatments and fragmenting treatments. Fragmenting treatments include mechanical, sonic, and hydrodynamic shearing. Repair treatments include nick repair via extension and/or ligation, polishing to create blunt ends, removal of damaged bases, such as deaminated, derivatized, abasic, or crosslinked nucleotides, etc. A nucleic acid molecule of interest may also be subjected to chemical modification (e.g., bisulfite conversion, methylation/demethylation), extension, amplification (e.g., PCR, isothermal, etc.), etc.

Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" may refer to nucleic acid(s) that are substantially complementary, as may be assessed by the same nucleotide comparison set forth above. The term "substantially complementary" may refer to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double-stranded nucleic acid molecule during hybridization. In certain embodiments, the term "substantially complementary" refers to at least one nucleic acid that may hybridize to at least one nucleic acid strand or duplex in stringent conditions. In certain embodiments, a "partially complementary" nucleic acid comprises at least one sequence that may hybridize in low stringency conditions to at least one single or double-stranded nucleic acid or contains at least one sequence in which less than about 70% of the nucleobase sequence is capable of base-pairing with at least one single or double-stranded nucleic acid molecule during hybridization.

The term "non-complementary" refers to nucleic acid sequence that lacks the ability to form at least one Watson-Crick base pair through specific hydrogen bonds.

The term "degenerate" as used herein refers to a nucleotide or series of nucleotides wherein the identity can be selected from a variety of choices of nucleotides, as opposed to a defined sequence. In specific embodiments, there can be a choice from two or more different nucleotides. In further specific embodiments, the selection of a nucleotide at one particular position comprises selection from only purines, only pyrimidines, or from non-pairing purines and pyrimidines.

The term "secondary structure" as used herein refers to the set of interactions between bases pairs. For example, in a DNA double helix, the two strands of DNA are held together by hydrogen bonds. The secondary structure is responsible for the shape that the nucleic acid assumes. For a single stranded nucleic acid, the simplest secondary structure is linear. For a linear secondary structure, no two subsequences of a nucleic acid molecule form an intramolecular structure stronger than −2 kcal/mol. As another example for a single stranded nucleic acid, one portion of the nucleic acid molecule may hybridize with a second portion of the same nucleic acid molecule, thereby forming a hairpin to stem loop secondary structure. For a non-linear secondary structure, at least two subsequences of a nucleic acid molecule from an intramolecular structure stronger than −2 kcal/mol.

As used herein, the term "subsequence" refers to a sequence of at least 5 contiguous base pairs.

"Sample" means a material obtained or isolated from a fresh or preserved biological sample or synthetically created source that contains nucleic acids of interest. Samples can include at least one cell, fetal cell, cell culture, tissue specimen, blood, serum, plasma, saliva, urine, tear, vaginal secretion, sweat, lymph fluid, cerebrospinal fluid, mucosa secretion, peritoneal fluid, ascites fluid, fecal matter, body exudates, umbilical cord blood, chorionic villi, amniotic fluid, embryonic tissue, multicellular embryo, lysate, extract, solution, or reaction mixture suspected of containing immune nucleic acids of interest. Samples can also include non-human sources, such as non-human primates, rodents and other mammals, other animals, plants, fungi, bacteria, and viruses.

As used herein in relation to a nucleotide sequence, "known" or "substantially known" refers to having sufficient sequence information in order to permit preparation of a nucleic acid molecule, including its amplification. This will typically be about 100%, although in some embodiments some portion of an adapter sequence is random or degenerate. Thus, in specific embodiments, substantially known refers to about 50% to about 100%, about 60% to about 100%, about 70% to about 100%, about 80% to about 100%, about 90% to about 100%, about 95% to about 100%, about 97% to about 100%, about 98% to about 100%, or about 99% to about 100%.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

II. TUBERCULOSIS AND DETECTION THEREOF

A. Tuberculosis

Tuberculosis (TB) is an infectious disease usually caused by *Mycobacterium tuberculosis* (MTB) bacteria. Tuberculosis generally affects the lungs, but it can also affect other parts of the body. Most infections show no symptoms, in which case it is known as latent tuberculosis. Around 10% of latent infections progress to active disease which, if left untreated, kill about half of those affected. Typical symptoms of active TB are chronic cough with blood-containing mucus, fever, night sweats, and weight loss. It was historically referred to as consumption due to the weight loss associated with the disease. Infection of other organs can cause a wide range of symptoms.

Tuberculosis is spread from one person to the next through the air when people who have active TB in their lungs cough, spit, speak, or sneeze. People with Latent TB do not spread the disease. Active infection occurs more often in people with HIV/AIDS and in those who smoke. Diagnosis of active TB is based on chest X-rays, as well as microscopic examination and culture of body fluids. Diagnosis of Latent TB relies on the tuberculin skin test (TST) or blood tests.

The main cause of TB is *Mycobacterium tuberculosis* (MTB), a small, aerobic, nonmotile *bacillus*. The high lipid content of this pathogen accounts for many of its unique clinical characteristics. It divides every 16 to 20 hours, which is an extremely slow rate compared with other bacteria, which usually divide in less than an hour. Mycobacteria have an outer membrane lipid bilayer. If a Gram stain is performed, MTB either stains very weakly "Gram-positive" or does not retain dye as a result of the high lipid and mycolic acid content of its cell wall. MTB can withstand weak disinfectants and survive in a dry state for weeks. In nature, the bacterium can grow only within the cells of a host organism, but *M. tuberculosis* can be cultured in the laboratory.

Using histological stains on expectorated samples from phlegm (also called sputum), scientists can identify MTB under a microscope. Since MTB retains certain stains even after being treated with acidic solution, it is classified as an acid-fast *bacillus*. The most common acid-fast staining techniques are the Ziehl-Neelsen stain and the Kinyoun stain, which dye acid-fast bacilli a bright red that stands out against a blue background. Auramine-rhodamine staining and fluorescence microscopy are also used.

The *M. tuberculosis* complex (MTBC) includes four other TB-causing mycobacteria: *M. bovis, M. africanum, M. canetti*, and *M. microti. M. africanum* is not widespread, but it is a significant cause of tuberculosis in parts of Africa. *M. bovis* was once a common cause of tuberculosis, but the introduction of pasteurized milk has almost eliminated this as a public health problem in developed countries. *M. canetti* is rare and seems to be limited to the Horn of Africa, although a few cases have been seen in African emigrants. *M. microti* is also rare and is seen almost only in immunodeficient people, although its prevalence may be significantly underestimated.

Other known pathogenic mycobacteria include *M. leprae, M. avium*, and *M. kansasii*. The latter two species are classified as "non-tuberculous mycobacteria" (NTM) or atypical mycobacteria. NTM causes neither TB nor leprosy, but they do cause lung diseases that resemble TB.

B. Detection

As mentioned above, smear microscopy using sputum samples is the standard of care for many areas with high TB incidence (8). Sputum culture also used as a diagnostic, particularly for drug sensitivity, but recent estimates suggest that 80-99.9% of all M.tb bacilli in sputum cannot be cultured under standard laboratory conditions, leading to gross under-estimations of bacillary loads by culture, especially in drug treated TB patients. Nucleic acid amplification-based tests for TB drug resistance genotypes (e.g., the Hain line-probe assay) have been in pathology labs for many years but require a culture step. In an effort to remove these culture requirements, the WHO has endorsed the PCR-based Cepheid GeneXpert MTB/RIF assay as a frontline diagnostic test for TB and for rifampicin resistance genotyping in endemic settings. However, despite having a claimed limit of detection of −130 M.tb bacilli/mL of sputum (closer to −1,000 M.tb bacilli/mL in real world settings), GeneXpert is not ideal because it has a sensitivity of −70% in smear negative TB patients, is unable to quantify bacillary load or monitor early bacteriocidal activity (9), and is relatively expensive (−$15/test, even with subsidies). In South Africa, the GeneXpert MTB/RIF sputum-based assay (Cepheid) has been the first-line TB diagnostic since 2011 (10). It relies upon amplification of a 192-base-pair target within the rpoB gene (11).

Urine is an ideal patient sample because it can be easily collected, is available in large volumes, and is relatively safe compared to alternative samples such as blood or sputum (3). Traditional TB diagnostic sensitivity is compromised because of difficulty producing sputum samples in HIV-infected patients (12-15) and children, together accounting for 72% of the TB incidence in South Africa (15). Additionally, patient willingness to provide samples and the improved sensitivity of molecular reagents has led to the detection of biomarkers from urine samples being increasingly used for diagnosis of infectious diseases, including *Escherichia coli* (16), leptospirosis (17), *Mycobacterium tuberculosis* (3), Dengue virus (18), Zaire Ebola virus (19), and Zika virus (20,21). Peters et al. (22) described detection of TB DNA biomarkers in urine as a potentially significant improvement to TB diagnosis, particularly if available in resource-limited countries. Several diagnostic assays are currently approved by the WHO utilizing urine specimens (15,23). Molecular testing using the GeneXpert® MTB/RIF is increasing in high disease burden areas (12,24,25), and has been evaluated using urine samples (26) but sensitivity is variable, particularly among HIV-infected patients (24,25,27,28). A rapid test for lipoarabinomannan (LAM) using a lateral flow assay has also been used as a TB diagnostic tool using urine specimens (4). This assay detects a component of the mycobacterial cell wall; however, it does not allow for quantification of the biomarker which is useful to determine the best course for treatment. The poor sensitivity of LAM testing, especially among HIV-uninfected patients makes it a less desirable biomarker (12,29). There is an urgent need for more rapid and simple nucleic acid based diagnostic tests to improve TB case detection and prevent further transmission of TB disease in developing countries (3,13,22,26). Many infectious diseases are diagnosed using PCR-based methods to detect a specific nucleic acid biomarker. In urine, these biomarkers are often degraded. Trends in DNA fragment length(30) from recent next-generation sequencing reports using urine sample DNA for diagnosis suggest that many more short fragments are present than previously thought. Some reports suggest significant numbers of fragments in the range of 29 to 45 bp in length (30,31), which is too short to be detected by traditional PCR assays. Urine fragmentation appears to be due at least in part to the action of DNases which degrade cell free DNA continuously (32,33). Much of the urine DNA studies and methodology are reviewed in Umansky (34) and urine fragment size and its influence on PCR have been discussed explicitly by Su (35). Recent work by Lutz' group has suggested that urine collected in the presence of EDTA has detectable IS6110 fragments (36-38). The pathway for transport of TB biomarkers to urine is illustrated in FIG. 1A.

There has been recent interest in detecting TB by using more easily obtained urine samples which has produced variable results. Several studies have detected TB nucleic acid biomarkers that have passed from the blood into urine (39), but others have failed to detect these biomarkers (3). Urine contains high concentrations of DNase I which randomly cleaves DNA into small fragments (30,33). If the nucleic acid biomarker is present in fragmented form, it is undetectable in urine by PCR methods if the target amplicon is missing one of the primer sites. In this disclosure, the inventors describe an alternative PCR methodology that can be used to detect nucleic acid fragments when the PCR target sequence is known but, because of DNA fragmentation, may not be present in a full-length form. PCR is one of the most sensitive diagnostics, but it has limited value if the targets are fragmented.

While shortening the amplicon length should theoretically increase the statistical likelihood of encountering the full-length target fragment in urine, it would have to be balanced with the tradeoff of the poor efficiency of a sub-optimal primer pair. Consequently, it is possible that a primer pair redesign may still result in reduced analytical sensitivity even if the target is present in a higher concentration.

Figure 2A:
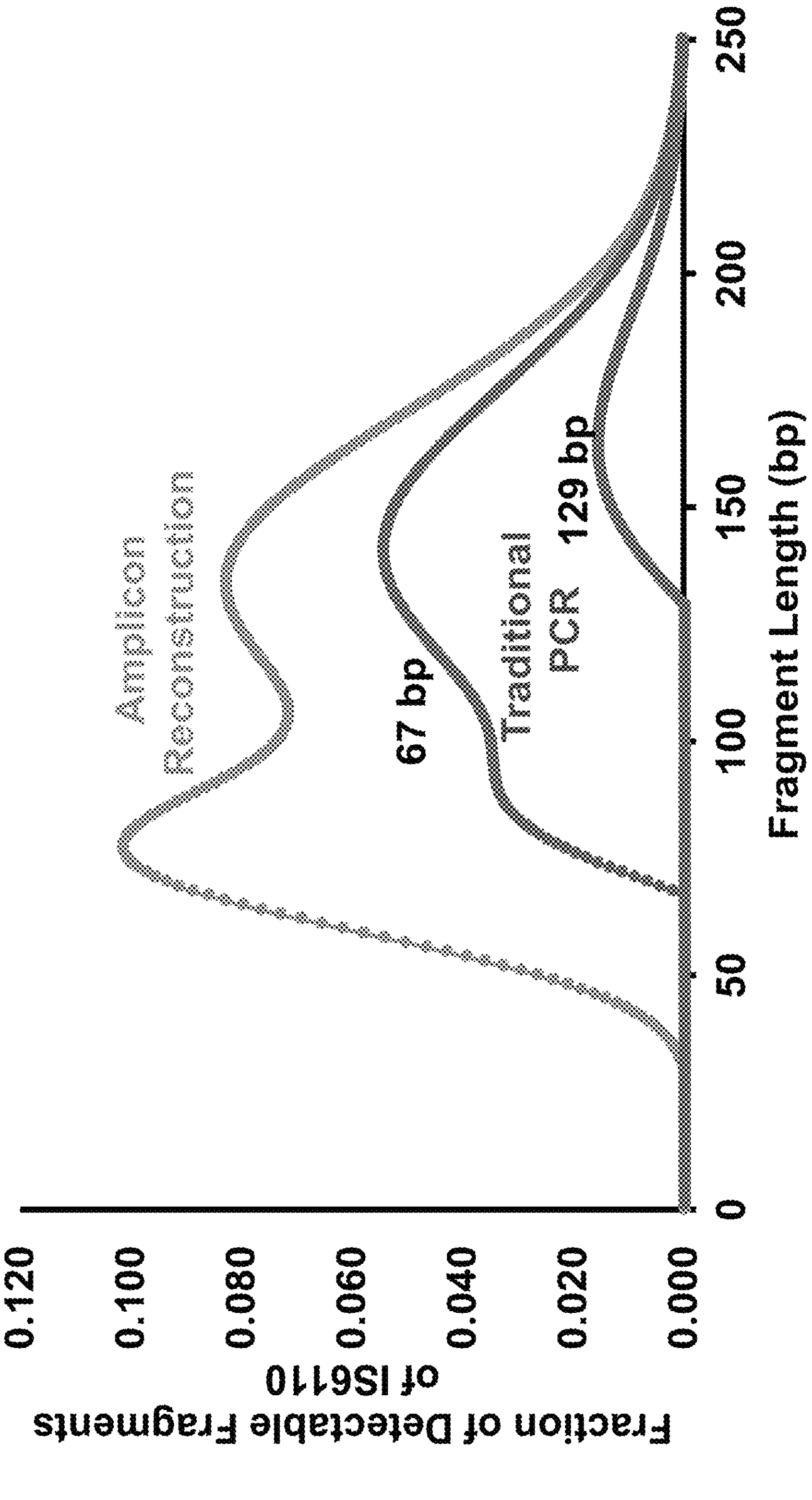
FIG. 2A. Estimate of the effect of the length of the target fragment on fragments detectable by both traditional PCR (blue) for PCR amplicons of length 129 and 67 bp and AR-PCR assuming a minimum detectable fragment length of 30 bp (orange).

To estimate the potential impact of fragment detection, the inventors sought the answer to the following question: "Over the range of expected IS6110 DNA fragments lengths, how does the fraction of IS6110 fragments detectable by the inventors' proposed amplicon reconstruction PCR method compared to the fraction detectable by traditional PCR?" To partially answer this, the distribution of transrenal DNA fragment length was approximated using a published data set on the fragmentation of DNA in urine (32) which found many fragments in the range of 50-100 base pairs. The maximum length considered was 250 base pairs. For each possible fragment length, the fraction of detectable fragments was calculated based on all possible fragments obtainable from the total sequence of IS6110. Based on a generalization of FIG. 2 of Su (35), a function for the fraction of detectable fragments was expressed as $(x-n+1)/(N-x+1)$ for $x>n$, and as 0 for $x<n$, where x is the length of the fragment, N is the total length of IS6110 gene, and n is the minimum length required for detection by either amplicon reconstruction PCR or traditional PCR. An approximation of the skewed fragment length distribution (32) was used to compute the $x>n$ values and FIG. 2A illustrates this relationship, showing the fraction of total fragments detectable as a function of fragment length for 1) a 30 bp detectable limit by reconstruction amplification PCR (upper orange curve) and 2) a 123 bp detectable limit imposed primer set spacing or 3) a 67-bp limit imposed primer set spacing in traditional PCR (lower blue curves). The calculation suggests that not only will targets be detectable at fragment lengths shorter than either amplicon length, but many more will also be detectable for fragments greater than either amplicon length.

III. APPLICATIONS

Potential applications for most infectious agents are envisioned since many of these have known unique genetic sequences that are eliminated from the blood stream through urinary secretion. Other types of detection applications include, for example, detection of a biomarker circulating in the blood that is associated with particular cancer. Some have been identified, but as more become known the method proposed here could serve as the detection platform.

IV. KITS

In still further embodiments, the present disclosure concerns kits for use with the methods described herein. The kit would contain one or more of (i) a nucleic acid template that partially hybridizes to and serves as an amplification template for a fragment of a nucleic acid target, (ii) one or more polymerases capable of extending the fragment once hybridized to said nucleic acid template, and (iii) a nucleotide tri-phosphate mixture, wherein adding is under conditions supporting extension of the fragment once hybridized to said nucleic acid template; The kits will thus comprise, in suitable container means, a one or more of the preceding reagents. In embodiments, two different polymerases may be included in the kit, for example, where one may be a U-tolerant DNA polymerase or is a heat sensitive polymerase. The nucleic acid template may comprise RNA or DNA uracil bases. The kit may also comprise and exonuclease.

The kits may further comprise a suitably aliquoted composition of the reagents mentioned above. The reagents of the kits may be packaged either in aqueous media or in lyophilized form. The container means of the kits will generally include at least one vial, test tube, flask, bottle, syringe or other container means, into which the reagents(s) may be placed, or preferably, suitably aliquoted. The kits of the present disclosure will also typically include a means for containing the various reagents in close confinement for commercial sale. Such containers may include injection or blow-molded plastic containers into which the desired vials are retained. Also contained in the kits may be instructions for preparation of reagents and use of the kits in methods described herein.

V. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

As discussed above, short RNA and DNA fragments are of increasing interest as biomarkers of nucleic acid processing and regulatory function, and the presence of infectious agents. The inventors are particularly interested in using urine as a patient sample for detection of fragments of a known biomarker sequence. A problem unique to this patient sample is the presence of DNases which degrade the DNA and RNA present in the sample into small fragments. Many of these fragments are thought to be too short (<40 base pairs) to be detectable by traditional PCR or RT-PCR. The reason they are undetectable is that the fragments present do not contain both primer regions and therefore the PCR primers cannot bind on both the upstream and downstream side of the amplicon region to produce the usual exponential growth required for sensitive detection.

Until recently the existence of TB DNA fragments in urine was controversial. Recent publications suggest that they are present and detectable if the urine sample is treated to block degradation (36-38). FIG. 1A shows a simple overview of the TB pulmonary infection and the presence of short fragments of DNA characteristic of TB present in urine. The inventors developed a small fragment detection method which reconstructs a full-length amplicon from DNA fragments. The method is based on including a capture template oligonucleotide that contains part of a known TB biomarker amplicon sequence. When DNA amplicon fragments bind to this extension oligonucleotide, target fragments are elongated, and a full-length amplicon containing both primer sites is created, which is subsequently amplified by traditional PCR. In this disclosure this process is referred to as amplicon reconstruction PCR and abbreviated AR-PCR.

Figure 1B:
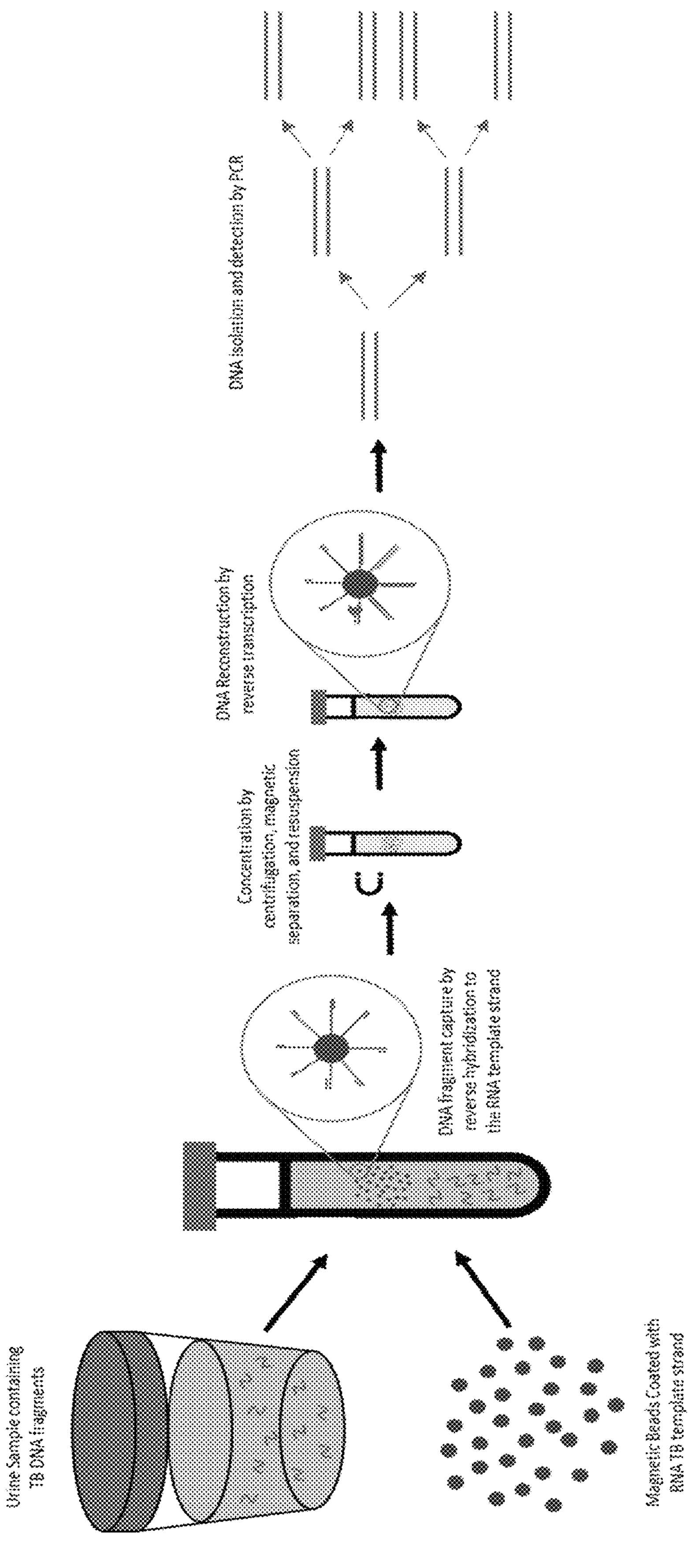
FIG. 1B. Schematic for fragment reconstruction based on optional magnetic bead separation and concentration using Design II.
Figure 6:
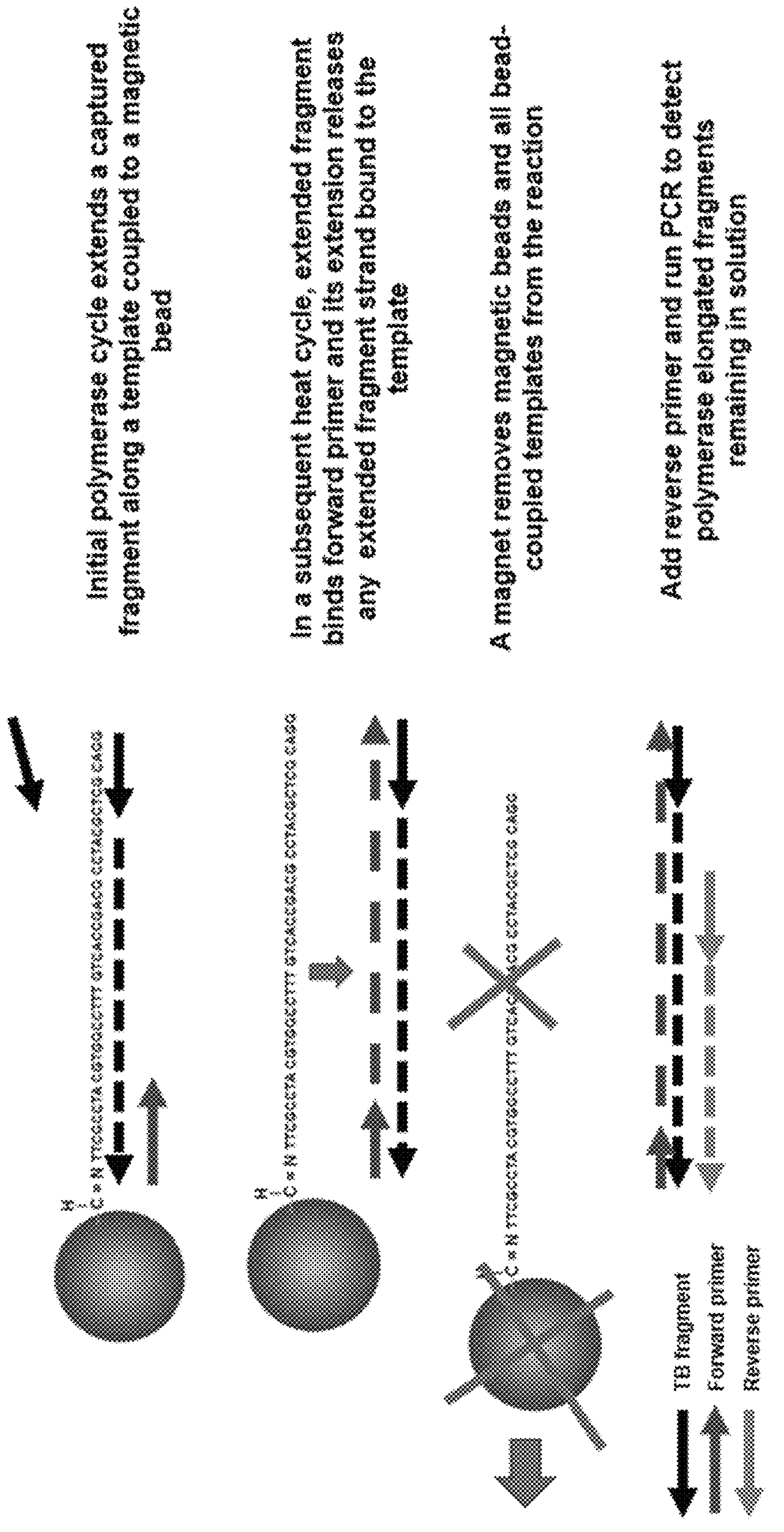
FIG. 6. Post-Capture Magnetic Removal of Template (Design IV). Capture template is bound to a magnetic bead and after fragment capture a magnet is used to concentrate the beads into a smaller volume. The template includes DNA bases (SEQ ID NO: 4). Complementary fragment to the template is extended by a DNA polymerase cycle. Forward primer also present in solution releases first cycle complement. Addition of reverse primer and subsequent PCR cycles detects extended fragments and not residual template.

FIG. 1B illustrates an overview of the sample collection to PCR output. In this illustration, fragment extension is achieved on the magnetic bead and the extended fragment is released from the template using Design IV (FIG. 6). In this design, after these initial steps the magnetic beads and template are removed to prevent template amplification in the subsequent PCR reaction.

Figure 2B:
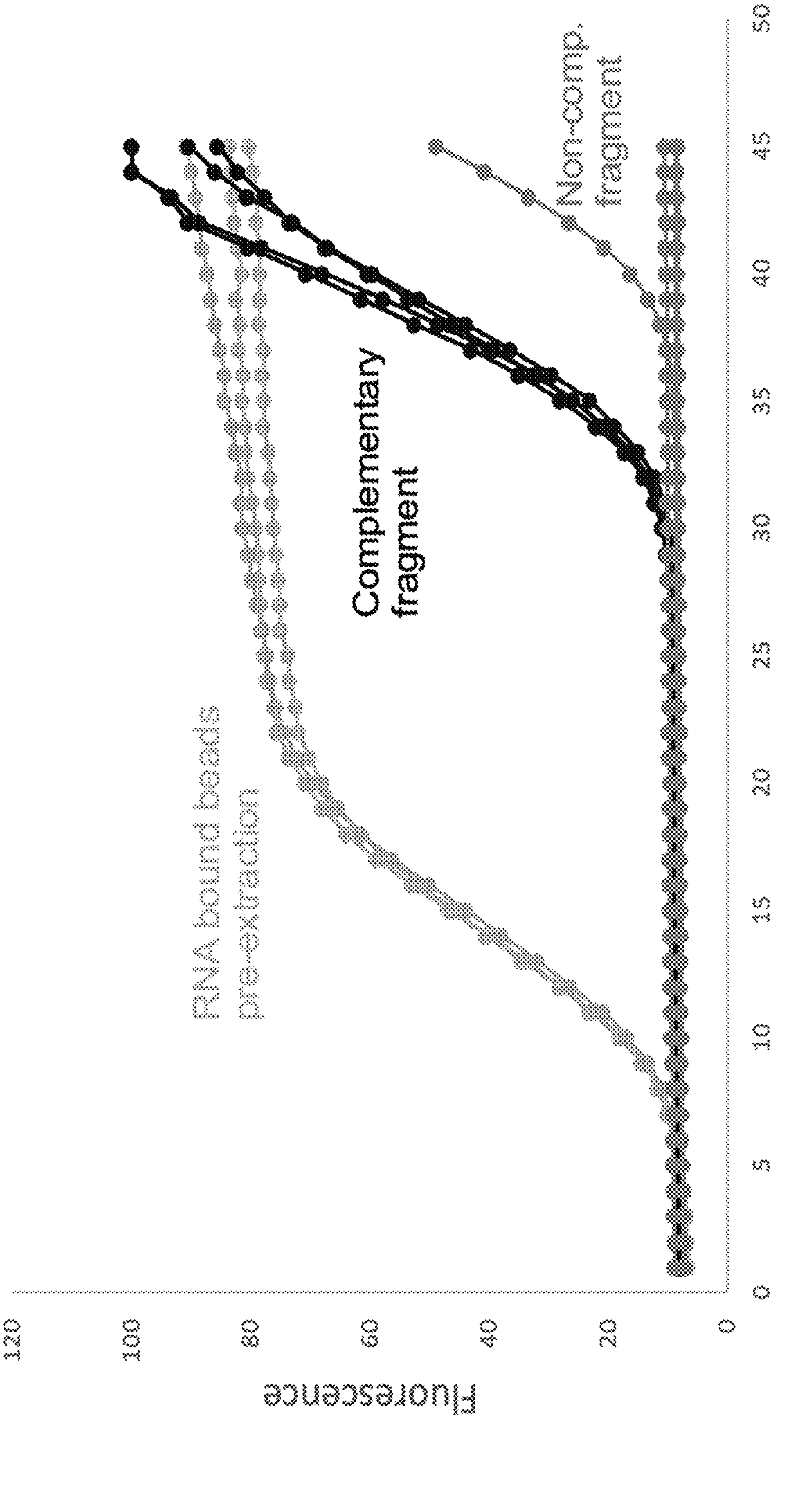
FIG. 2B. Differential detection of complementary fragment vs a non-complementary fragment using the design shown in FIG. 1B.

FIG. 2B shows an example PCR result illustrating how complementary fragments are preferentially amplified over non-complementary fragments. This is illustrative of a general method for the detection of TB DNA fragments using "amplicon reconstruction," which is described as Design IV, is shown in FIG. 6. The method creates full-length target sequences if partial sequences of the TB biomarker target are present in a sample. To achieve this, the inventors add a capture template designed to partially hybridize and serve as a template for fragment elongation by a polymerase. Also present in the reaction is a forward primer. Using a normal PCR master mix, when fragments are present they act as reverse primers and, this results in what is often referred to as asymmetric PCR (40). Here, the reverse primer is in very low concentrations and each round of PCR increases the number of extended copies linearly. At the same time, the presence of the forward primer serves to separate the extended fragment (anti-sense strand) from the capture template coupled to the magnetic bead. This released sense strand is then left in solution after magnetic bead removal and, when a normal concentration of reverse primer is added, is amplified exponentially and detected by PCR.

Figure 3:
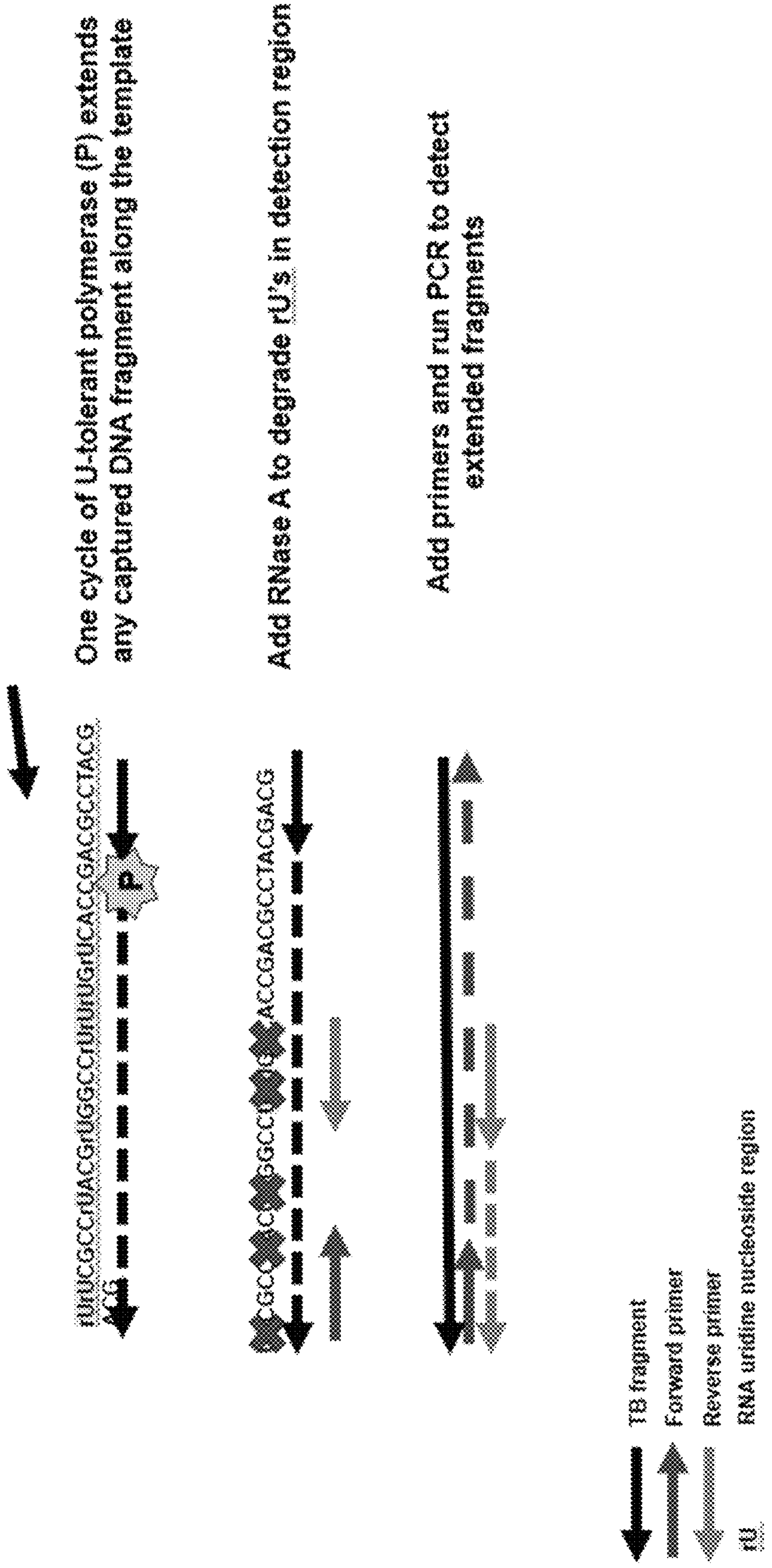
FIG. 3. Post-Capture Degradation of Detection Region of Template (Design I). RNA base rU is incorporated in the capture sequence (SEQ ID NO: 1). A complementary fragment to the template is extended by DNA polymerase. Addition of RNase A degrades the capture template. Adding PCR primers detects extended fragments and not residual template.
Figure 4:
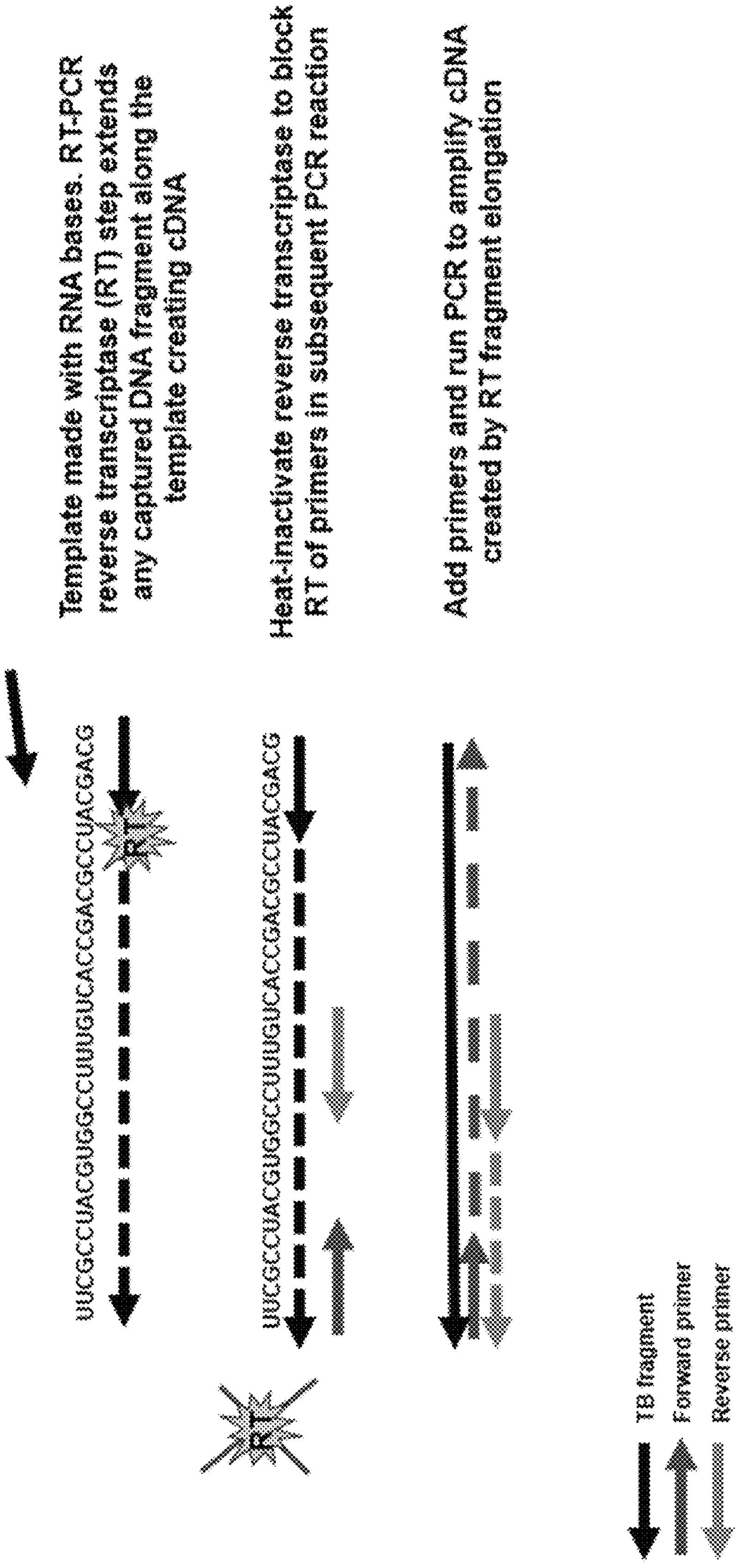
FIG. 4. Post-Capture Blockage of Reverse Transcription Along Template (Design II). The template is made up of only RNA bases (SEQ ID NO: 2). Complementary fragment to the template is extended by reverse transcriptase. Addition of RNase A degrades the template. Adding PCR primers detects extended fragments and not residual template.
Figure 5:
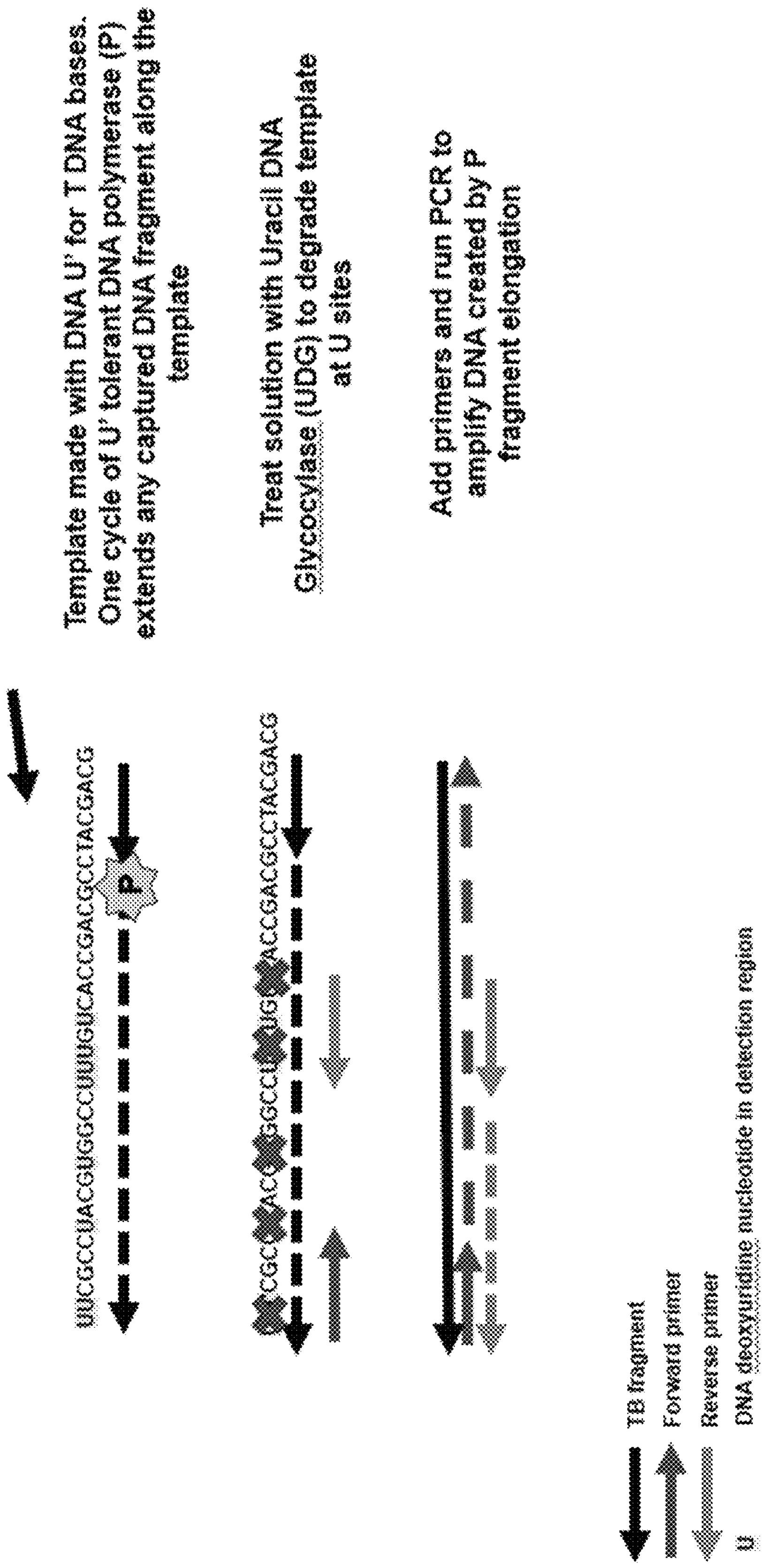
FIG. 5. Post-Capture Degradation of PCR Amplification Region of Template (Design III). The template includes DNA deoxyuridine bases (SEQ ID NO: 3). A complementary fragment to the template is extended by DNA polymerase. Addition of uracil DNA glycocylase degrades the template. Adding PCR primers detects extended fragments and not residual template.

The method should be applicable to many fragments of TB nucleic acid biomarkers and, for any given sample, the limit of detection should improve. Modifications of the method shown in FIG. 6 that also include a degradation step to account for capture template released from the magnetic beads during processing were also developed. As shown in FIG. 3, a post-capture and degradation of detection region of template is described in Design I. Here RNA base rU is incorporated in the capture sequence. A complementary fragment to the template is extended by DNA polymerase. Addition of RNase A degrades the capture template. Addition PCR primers detects extended fragments and not residual template. As shown in FIG. 4, a post-capture blockage of reverse transcription along template is described in Design II. Here the template is made up of only RNA bases. Complementary fragment to the template is extended by reverse transcriptase. Addition of RNase A degrades the template. Adding PCR primers detects extended fragments and not residual template. As shown in FIG. 5, a post-capture degradation of PCR amplification region of template is described in Design III. Here the template includes DNA deoxyuridine bases. A complementary fragment to the template is extended by DNA polymerase. Addition of uracil DNA glycocylase degrades the template. Adding PCR primers detects extended fragments and not residual template.

Figure 7:
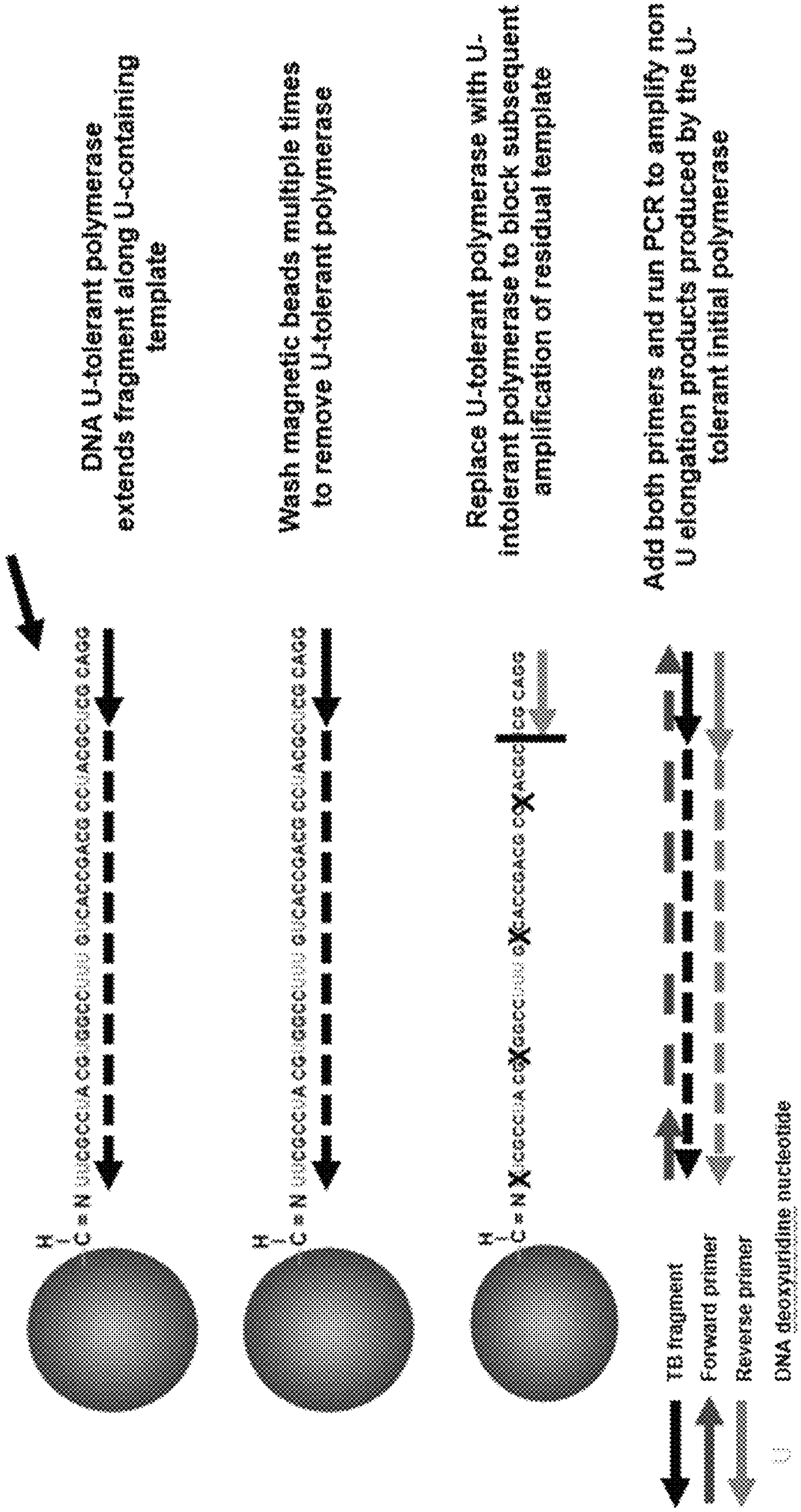
FIG. 7. Post-Magnetic Washing "Capture" to Enable Polymerase Exchange (Design V). Capture template incorporating deoxyuridine (SEQ ID NO: 5) is bound to a magnetic bead and after fragment capture a magnet is used to concentrate the beads into a smaller volume. Complementary fragment to the template is extended by a U-tolerant DNA polymerase cycle. Magnetic capture and washing removes U-tolerant polymerase. Addition of U-intolerant polymerase, reverse primer and subsequent PCR cycles detects extended fragments and not residual U-containing template.

FIG. 7 illustrates Design IV which is based on switching between an initial U-tolerant polymase for the initial fragment reaction and a U-intolerant polymerase for the final PCR product amplification reaction. In this design the template contains deoxyuridine nucleotides and a U-tolerant polymerase such as EpiMark® Hot Start Taq DNA Polymerase (M0490S, New England BioLabs) is used to extend fragments. After extension, double-stranded product attached to magnetic beads is washed to remove the U-tolerant polymerase. After rinsing primers and a U-intolerant polymerase such as Q5 ® High-Fidelity DNA Polymerase (M0491S, New England BioLabs) is added and the extended fragment strand is amplified. U-containing original template is not amplified.

PCR will not amplify a DNA sequence if it does not contain both of the primers. In some cases, fragmented DNA from the original full-length target may be present but are partially degraded by other biological processes. These will not be detected by PCR. The novel element here is the addition of sequences that are complementary to the fragments of the target amplicon that are extended by the PCR polymerase during the course of a normal PCR heat/cool cycle to extend the fragmented double-stranded DNA so that the reaction now contains full length PCR amplicons that can be amplified subsequently during a normal PCR reaction. In other words, this method supplies reagents that interface with the enzymes, primers and fragmented DNA present in the reaction that will enable the detection of a fragmented nucleic acid biomarker.

A number of previous reports have investigated the use of fragmented DNA. These include disclosures for amplification of fragmented (ancient) DNA (41), studies on mechanism of molecular evolution (42) and forensics (43). What these techniques have in common is the necessity of creating longer DNA fragments from shorter ones for downstream molecular biology disclosures. This is often accomplished by ligating either linkers or other fragments to each other to create longer fragments. Another approach is to perform PCR without primers, which results in global amplification of all DNA fragments (42,43). However, the major drawback of these techniques is that they do not provide gene-specific enrichment. While it is difficult to identify an exact precedent for this strategy, a technique that has a similar goal is Rapid Amplification of cDNA Ends (RACE), which is used to clone a gene when only part of the sequence is known. For example, this is often performed to gather information regarding transcription initiation sites. In one common approach an RNA linker is added to the 5' end of the mRNA target and the other primer is designed using the known sequence. Consequently, only one gene-specific primer is required (44). However, the RACE approach requires an additional step that is different from the inventors' proposed strategy: appendage of a linker to the target. This requires other enzymatic reactions, including ligation. Instead, this approach only requires one enzyme and one tube for the entire process. Additionally, RACE and PCR without primers have lower specificity because at most, only one gene-specific primer is used. In RACE, the second primer site is added in the form of an RNA linker in an indiscriminate fashion because there is no selection for the target of interest during ligation. For a molecular diagnostic to be useful, it must be sensitive as well as specific. A major benefit of the strategy outlined in this disclosure is its specificity—only fragments that contain a specific portion of the IS6110 amplicon will be targeted for AR-PCR even if the amplicon is fragmented. Recent work by Lutz et al (36-38) has shown that when a urine sample is collected with additives (EDTA) that block the action of DNase activity a magnetic bead functionalized with a sequence complementary to IS6110 can be used to capture fragmented IS6110 and these fragments are detectable by subsequent PCR. This work provides confirmation of the existence of IS6110 fragments in urine. The inventors' prior work (45) did not use an EDTA additive, confirmed DNase activity in all samples and consequently detection was only possible in HIV patients with TB.

Figure 8:
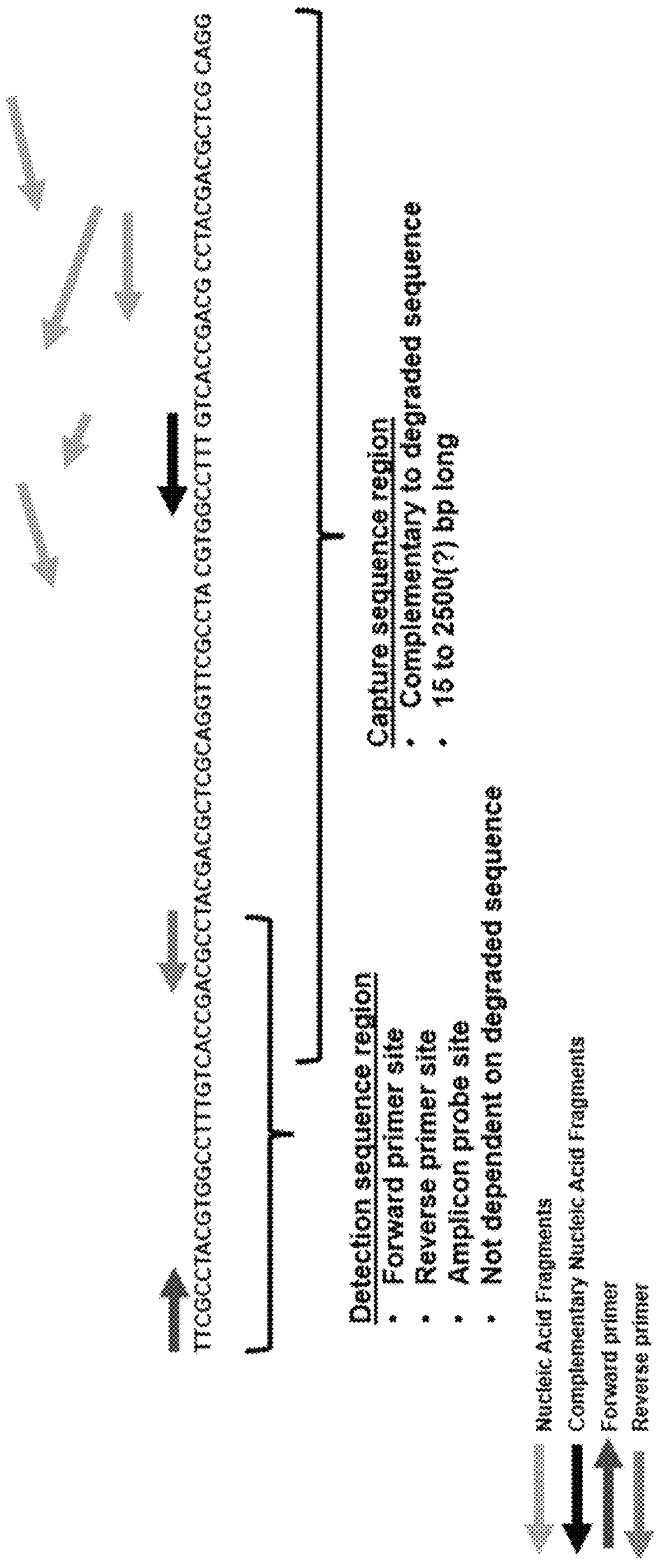
FIG. 8. PCR and Capture Features of the Nucleic Acid Template. Template (SEQ ID NO: 6) contains a detection region sequence (left) with forward and reverse primer sequences and a capture sequence (right) with complementarity to the intact sequence of interest. The two regions may overlap. Only complementary fragments are hybridized and extended by polymerase to create a second strand containing the two primer sites.

FIG. 8 illustrates certain features of the capture template design. These design elements are included as a way to fulfill the required properties needed in this assay. These properties are 1) specific capture of biomarker fragments, 2) a means to remove the capture template and prevent its "bleed-through" into the final PCR detection reaction, and 3) compatibility with standard PCR procedures. The first is achieved by designing a nucleic acid sequence that contains a region with reverse complementarity to the sequence of the known biomarker. As illustrated, this also contains a spacer region between the capture sequence and the 5' end (left side here) that couples to the separation moiety (shown here as a magnetic bead). In the figure the 3' end (right side) contains the reverse complement sequence and the 5' end contains two primer regions (reverse primer & forward primer) that comprise the region amplified during subsequent PCR. These can also overlap with the biomarker sequence, but here are shown as contiguous. These primer sites are designed to meet the third requirement. Requirement two in this design is achieved by magnetically to remove the capture template but could be done more generally by a glass bubble or some forward primer moiety that enables separation of a subsequent sense strand. 'Bleed-through" of the capture template (meaning be present in the PCR solution after the beads have been removed) will produce background signal even when no fragment is present and this must be minimized. One way to do this is the design of the capture template is to incorporate U's instead of T's in the sequence. As is done in some commercial PCR kits, prior to the PCR reaction, a degradation enzyme is activated to inactivate the polymerase copying of any sequence containing U's. Examples of this design are illustrated in FIG. 3 and FIG. 5. Some of the Luna kits are designed with this in mind to reduce carryover from PCR reactions that would otherwise contaminate the PCR reaction. Here the inventors are using a similar idea in a different application.

Figure 9:
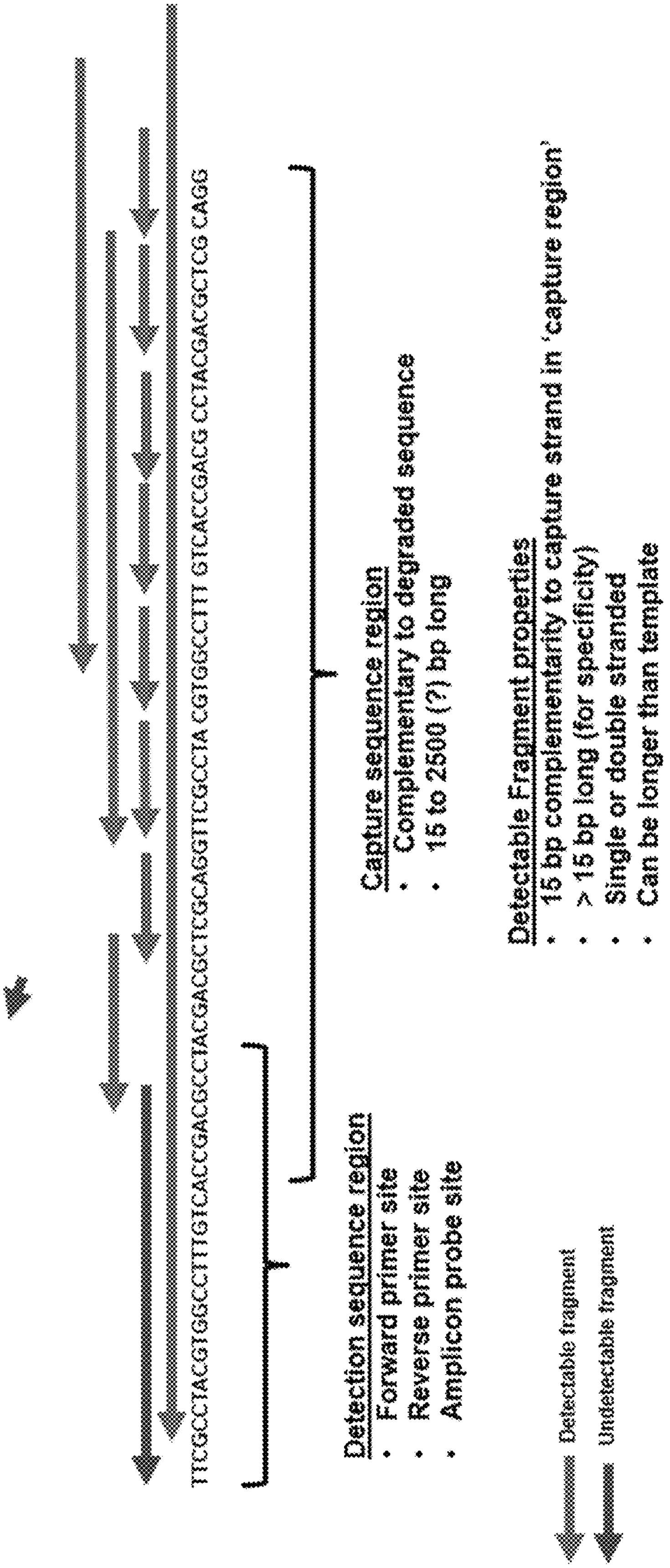
FIG. 9. Degradation Fragments Detectable. All method designs proposed require specific hybridization as the first step. Shown schematically here in green are the binding fragments that will bind and be successfully extended. These are those with a minimum specificity length (anticipated to be 10 to 15 bases) that have a 3' end that binds either upstream of the reverse primer site or a 3' end that binds between the primer sites and a 5' end that binds upstream of the reverse primer site. Shown schematically in red are two cases that fail. Either a fragment that is too short that it will not bind at the specified temperature or a fragment that binds within the primer sites but does not span the reverse primer site.
Figure 10:
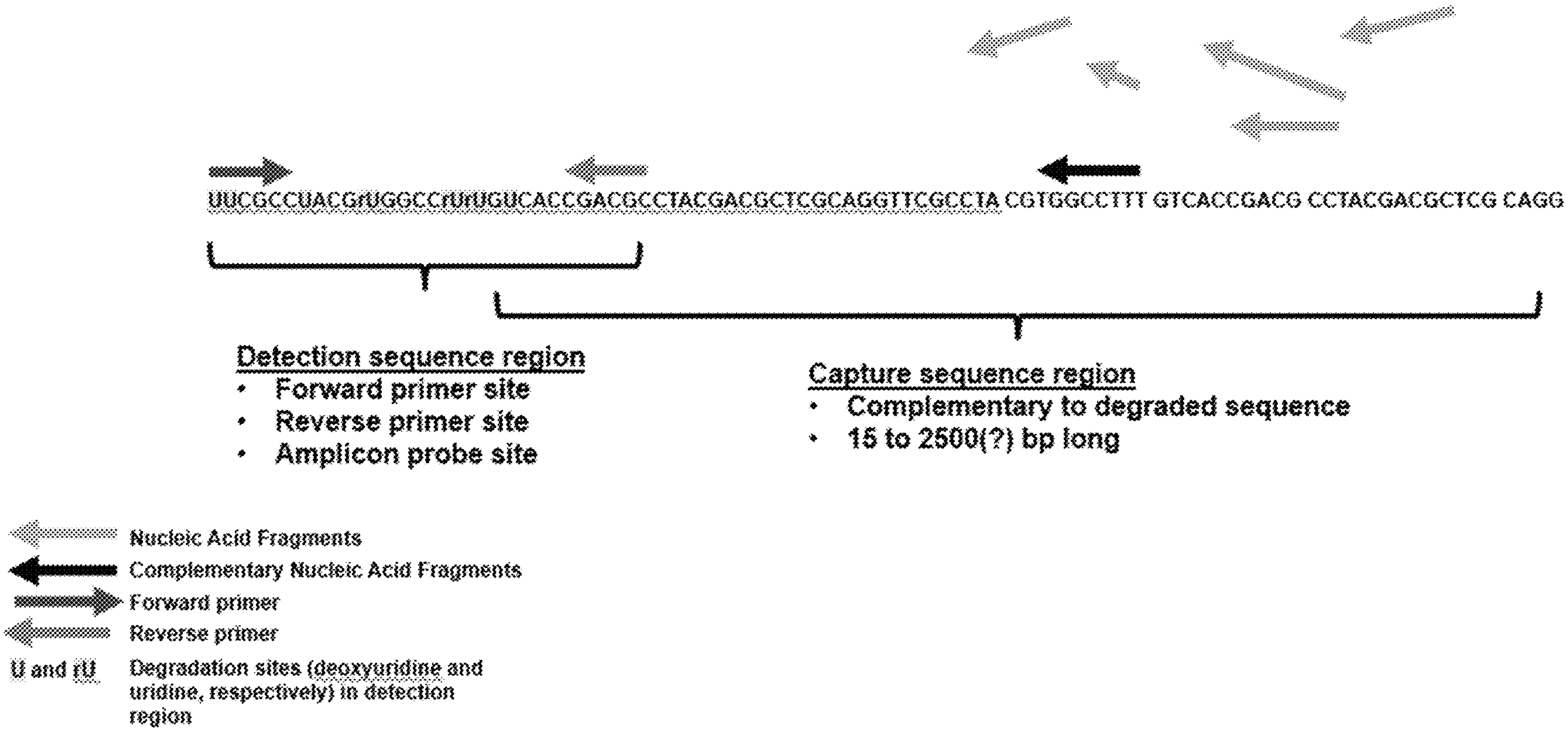
FIG. 10. Degradation Features of the Nucleic Acid Template. Deoxyuridine or uridine bases are incorporated within the detection sequence of the capture strand (SEQ ID NO: 7). These sites are used to degrade the template after fragment capture to avoid template amplification in the subsequent PCR reaction.
Figure 11:
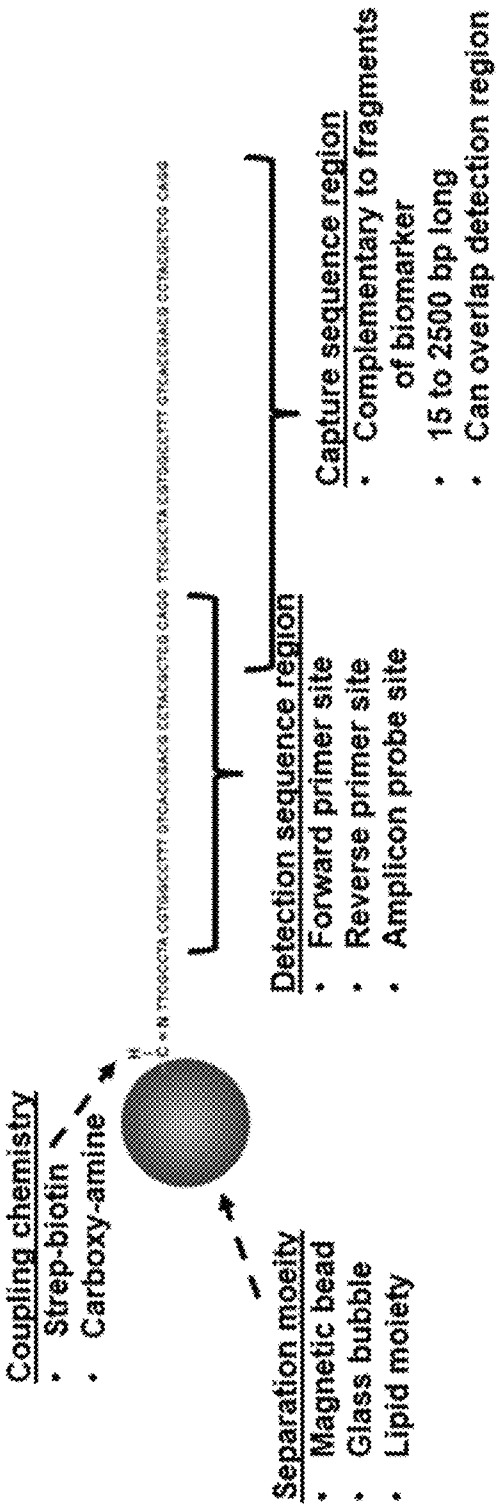
FIG. 11. Processing/Separation Features of the Nucleic Acid Template Used in Designs IV and V. To enable concentration and subsequent processing steps templates are coupled via well-known coupling chemistries to physical materials or a chemical structure that permits subsequent processing of the template bound to a complementary fragment or its extension.

Many of the characteristic features of this general approach and further described in FIGS. 9, 10 and 11. FIG. 9 illustrate the types of degradation fragments detectable by these approaches. All methods designs proposed require specific hybridization as the first step. Shown schematically here in green are the binding fragments that will bind and be successfully extended. These are those with a minimum specificity length (anticipated to be 10 to 15 bases) that have a 3' end that binds either upstream of the reverse primer site or a 3' end that binds between the primer sites and a 5' end that binds upstream of the reverse primer site. Shown schematically in red are two cases that fail. Either a fragment that is too short that it will not bind at the specified temperature or a fragment that binds within the primer sites but does not span the reverse primer site. Not shown are fragments without any complementarity to the template. These do not bind and are not extended. FIG. 10 illustrates some of the degradation features incorporated into several designs. Deoxyuridine or uridine bases are incorporated within the detection sequence of the capture strand. These sites are used to degrade the template after fragment capture to avoid template amplification in the subsequent PCR reaction. FIG. 11 illustrates processing/separation features of the nucleic acid template examples of which are incorporated in Designs IV and V. To enable concentration and subsequent processing steps, templates are coupled via well-known coupling chemistries to physical materials or a chemical structure that permits subsequent processing of the template bound to a complementary fragment or its extension.

In the design proposed here, the inventors build upon the observation that TB biomarkers are present in urine. However, the use of EDTA to block degradation may in fact reduce fragment detectability. In the methods proposed here, the inventors design methods that depend on fragmentation to produce a sufficient signal for detection. Up to a limit, more fragmentation produces more sequences, each of which can trigger a template reconstruction event. This limit is around 10 to 15 base segments. Sequences shorter than that are not unique. Conveniently, this design can be implemented at temperatures that prevent binding of these non-specific sequences by performing the fragment—capture template binding step at a temperature above 60° C. or so. This reduces the need for the presence of EDTA treatment of the urine and matches better with current urine collection practices.

The diagnosis of tuberculosis is most often achieved using a sputum sample. Many patients are not able to produce sputum (e.g., children) but non-invasive collection of urine is readily achievable. Several studies have shown that urine contains fragments of DNA and RNA that have passed from the blood into urine which some have begun to detect and characterize by using sequencing technologies. Unfortunately, sequencing is not available in many locations where the initial diagnosis and subtyping of the bacterial species is needed most. Thus, the alternative PCR methodology described herein that can be used to detect nucleic acid fragments when a known target sequence is present has tremendous value in general, but in particular in the diagnosis of TB. As such, in addition to TB testing in urine, this technology could also be used to detect any known biomarker that has been partially degraded through RNase or DNase activity. Potential applications for most infectious agents are envisioned since many of these have known unique genetic sequences that are eliminated from the blood stream through urinary secretion. Other types of detection applications include, for example, detection of a biomarker circulating in the blood that is associated with particular cancer. Some have been identified, but as more become known the method proposed here could serve as the detection platform.

This approach not only takes advantage of the high sensitivity and specificity inherent in the PCR methodology, but also the widespread availability of PCR instrumentation already in use in many settings for other diagnostic procedures. As such, the implementation of this technology could be rapid and universal.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

1. Organization, W. H. (2018) Global tuberculosis report 2018.
2. Organization, W. H. (2011) The Global Plan to Stop TB (2011-2015): Transforming the Fight Towards Elimination of Tuberculosis.
3. Green, C., Huggett, J. F., Talbot, E., Mwaba, P., Reither, K., and Zumla, A. I. (2009) Rapid diagnosis of tuberculosis through the detection of mycobacterial DNA in urine by nucleic acid amplification methods. The Lancet. Infectious diseases 9, 505-511
4. Peter, J. G., Zijenah, L. S., Chanda, D., Clowes, P., Lesosky, M., Gina, P., Mehta, N., Calligaro, G., Lombard, C. J., Kadzirange, G., Bandason, T., Chansa, A., Liusha, N., Mangu, C., Mtafya, B., Msila, H., Rachow, A., Hoelscher, M., Mwaba, P., Theron, G., and Dheda, K. (2016) Effect on mortality of point-of-care, urine-based lipoarabinomannan testing to guide tuberculosis treatment initiation in HIV-positive hospital inpatients: a pragmatic, parallel-group, multicountry, open-label, randomised controlled trial. Lancet 387, 1187-1197
5. WHO. (2018) Global Tuberculosis Report 2018., Geneva, Switzerland
6. Organization, W. H. (2018) South Africa. Tuberculosis Profile.
7. Ismail, N. A., Omar, S. V., Joseph, L., Govender, N., Blows, L., Ismail, F., Koomhof, H., Dreyer, A. W., Kaniga, K., and Ndjeka, N. (2018) Defining Bedaquiline Susceptibility, Resistance, Cross-Resistance and Associated Genetic Determinants: A Retrospective Cohort Study. EBioMedicine 28, 136-142
8. Cambanis, A., Ramsay, A., Wlrkom, V., Tata, E., and Cuevas, L. E. (2007) Investing time in microscopy: an opportunity to optimise smear-based case detection of tuberculosis. The international journal of tuberculosis and lung disease: the official journal of the International Union against Tuberculosis and Lung Disease 11, 40-45
9. Kayigire, X. A., Friedrich, S. 0., Venter, A., Dawson, R., Gillespie, S. H., Boeree, M. J., Heinrich, N., Hoelscher, M., Diacon, A. H., and Pan African Consortium for the Evaluation of Anti-tuberculosis, A. (2013) Direct comparison of Xpert MTB/RIF assay with liquid and solid mycobacterial culture for quantification of early bactericidal activity. Journal of clinical microbiology 51, 1894-1898
10. World Health Organization. Global tuberculosis report 2013. Geneva
11. Lawn, S. D., and Nicol, M. P. (2011) Xpert® MTB/RIF assay: development, evaluation and implementation of a new rapid molecular diagnostic for tuberculosis and rifampicin resistance. Future Microbial 6, 1067-1082
12. Englen, M. D., and Kelley, L. C. (2000) A rapid DNA isolation procedure for the identification of *Campylobacter jejuni* by the polymerase chain reaction. Letters in applied microbiology 31, 421-426
13. Davids, M., Dheda, K., Pant Pai, N., Cogill, D., Pai, M., and Engel, N. (2015) A Survey on Use of Rapid Tests and Tuberculosis Diagnostic Practices by Primary Health Care Providers in South Africa: Implications for the Development of New Point-of-Care Tests. PloS one 10, e0141453
14. Peter, J. G., Theron, G., and Dheda, K. (2012) Urine antigen test for diagnosis of HIV-associated tuberculosis. The Lancet. Infectious diseases 12, 825; author reply 826-827
15. WHO. (2013) Xpert MTB/RIF assay for the diagnosis of pulmonary and extrapulmonary TB in adults and children., World Health Organization, Geneva, Switzerland
16. van der Zee, A., Roorda, L., Bosman, G., and Ossewaarde, J. M. (2016) Molecular Diagnosis of Urinary Tract Infections by Semi-Quantitative Detection of Uropathogens in a Routine Clinical Hospital Setting. PloS one 11, e0150755
17. Iwasaki, H., Chagan-Yasutan, H., Leana, P. S., Koizumi, N., Nakajima, C., Taurustiati, D., Hanan, F., Lacuesta, T. L., Ashino, Y., Suzuki, Y., Gloriani, N. G., Telan, E. F., and Hattori, T. (2016) Combined antibody and DNA detection for early diagnosis of leptospirosis after a disaster. Diagn Microbial Infect Dis 84, 287-291
18. Andries, A. C., Duong, V., Ly, S., Cappelle, J., Kim, K. S., Lam Try, P., Ros, S., Ong, S., Huy, R., Horwood, P., Flamand, M., Sakuntabhai, A., Tarantola, A., and Suchy, P. (2015) Value of Routine Dengue Diagnostic Tests in Urine and Saliva Specimens. PLoS Negl Trap Dis 9, e0004100
19. Southern, T. R., Racsa, L. D., Albarino, C. G., Fey, P. D., Hinrichs, S. H., Murphy, C. N., Herrera, V. L., Sambol, A. R., Hill, C. E., Ryan, E. L., Kraft, C. S., Campbell, S., Sealy, T. K., Schuh, A., Ritchie, J. C., Lyon, G. M., 3rd, Mehta, A. K., Varkey, J. B., Ribner, B. S., Brandy, K. P., Stroher, U., lwen, P. C., and Burd, E. M. (2015) Comparison of FilmArray and Quantitative Real-Time Reverse Transcriptase PCR for Detection of Zaire Ebolavirus from Contrived and Clinical Specimens. Journal of clinical microbiology 53, 2956-2960

20. Gourinat, A. C., O'Connor, 0., Galvez, E., Goarant, C., and Dupont-Rouzeyrol, M. (2015) Detection of Zika virus in urine. Emerg Infect Dis 21, 84-86
21. Euliano, E. M., Hardcastle, A. N., Victoriano, C. M., Gabella, W. E., Haselton, F. R., and Adams, N. M. (2019) Multiplexed Adaptive RT-PCR Based on L-DNA Hybridization Monitoring for the Detection of Zika, Dengue, and Chikungunya RNA. Sci Rep 9, 11372
22. Peter, J., Green, C., Hoelscher, M., Mwaba, P., Zumla, A., and Dheda, K. (2010) Urine for the diagnosis of tuberculosis: current approaches, clinical applicability, and new developments. Current opinion in pulmonary medicine 16, 262-270
23. WHO. (2015) The use of lateral flow urine lipoarabinomannan assay (LF-LAM) for the diagnosis and screening of active tuberculosis in people living with HIV. Geneva, Switzerland
24. Bjerrum, S., Kenu, E., Lartey, M., Newman, M. J., Addo, K. K., Andersen, A. B., and Johansen, I. S. (2015) Diagnostic accuracy of the rapid urine lipoarabinomannan test for pulmonary tuberculosis among HIV-infected adults in Ghana-findings from the DETECT HIV-TB study. BMC infectious diseases 15, 407
25. Lacourse, S. M., Cranmer, L. M., Materna, D., Kinuthia, J., Richardson, B. A., John-Stewart, G., and Horne, D. J. (2016) Tuberculosis Case Finding in HIV-Infected Pregnant Women in Kenya Reveals Poor Performance of Symptom Screening and Rapid Diagnostic Tests. Journal of acquired immune deficiency syndromes 71, 219-227
26. Dheda, K., Barry, C. E., 3rd, and Maartens, G. (2016) Tuberculosis. Lancet 387, 1211-1226
27. Lawn, S. D., Kerkhoff, A. D., Burton, R., Schutz, C., van Wyk, G., Vogt, M., Pahlana, P., Nicol, M. P., and Meintjes, G. (2015) Rapid microbiological screening for tuberculosis in HIV-positive patients on the first day of acute hospital admission by systematic testing of urine samples using Xpert MTB/RIF: a prospective cohort in South Africa. BMC medicine 13, 192
28. Peter, J. G., Theron, G., Muchinga, T. E., Govender, U., and Dheda, K. (2012) The diagnostic accuracy of urine-based Xpert MTB/RIF in HIV-infected hospitalized patients who are smear-negative or sputum scarce. PloS one 7, e39966
29. HaMa, Y., Fielding, K. L., Chihota, V. N., Adonis, L., Charalambous, S., Karstaedt, A., McCarthy, K., Nicol, M. P., Ndlovu, N. T., Sahid, F., Churchyard, G. J., and Grant, A. D. (2016) Diagnostic Accuracy of Lateral Flow Urine LAM Assay for TB Screening of Adults with Advanced Immunosuppression Attending Routine HIV Care in South Africa. PloS one 11, e0156866
30. Markus, H., Zhao, J., Contente-Cuomo, T., Raupach, E., Odenheimer-Bergman, A., Connor, S., McDonald, B. R., Hutchins, E., McGilvery, M., de la Maza, M. C., Van Keuren-Jensen, K., Pirrotte, P., Goel, A., Becerra, C., Von Hoff, D. D., Celinski, S. A., Hingorani, P., and Murtaza, M. (2019) Sub-nucleosomal organization in urine cell-free DNA. bioRxiv, 696633
31. Tsui, N. B., Jiang, P., Chow, K. C., Su, X., Leung, T. Y., Sun, H., Chan, K. C., Chiu, R. W., and Lo, Y. M. (2012) High resolution size analysis of fetal DNA in the urine of pregnant women by paired-end massively parallel sequencing. PloS one 7, e48319
32. Cheng, T. H. T., Jiang, P., Tam, J. C. W., Sun, X., Lee, W. S., Yu, S. C. Y., Teoh, J. Y. C., Chiu, P. K. F., Ng, C. F., Chow, K. M., Szeto, C. C., Chan, K. C. A., Chiu, R. W. K., and Lo, Y. M. D. (2017) Genomewide bisulfile sequencing reveals the origin and time-dependent fragmentation of urinary cfDNA. Clin Biochem 50, 496-501
33. Nadano, D., Yasuda, T., and Kishi, K. (1993) Measurement of deoxyribonuclease I activity in human tissues and body fluids by a single radial enzyme-diffusion method. Clin Chem 39, 448-452
34. Umansky, S. R., and Tomei, L. D. (2007) Transrenal DNA testing: progress and perspectives. Expert Review of Molecular Diagnostics 6
35. Su, Y. H., Wang, M., Block, T. M., Landt, 0., Botezatu, I., Serdyuk, 0., Lichtenstein, A., Melkonyan, H., Tomei, L. D., and Umansky, S. (2004) Transrenal DNA as a diagnostic tool: important technical notes. Ann NY Acad Sci 1022, 81-89
36. Oreskovic, A., Waalkes, A., Holmes, E. A., Rosenthal, C. A., Wilson, D. P. K., Shapiro, A. E., Drain, P. K., Lutz, B. R., and Salipante, S. J. (2021) Characterizing the molecular composition and diagnostic potential of *Mycobacterium tuberculosis* urinary cell-free DNA using next-generation sequencing. Int J Infect Dis 112, 330-337
37. Oreskovic, A., and Lutz, B. R. (2021) Ultrasensitive hybridization capture: Reliable detection of <1 copy/ml short cell-free DNA from large-volume urine samples. PloS one 16, e0247851
38. Oreskovic, A., Panpradist, N., Marangu, D., Ngwane, M. W., Magcaba, Z. P., Ngcobo, S., Ngcobo, Z., Home, D. J., Wlison, D. P. K., Shapiro, A. E., Drain, P. K., and Lutz, B. R. (2021) Diagnosing Pulmonary Tuberculosis by Using Sequence-Specific Purification of Urine Cell-Free DNA. Journal of clinical microbiology 59, e0007421
39. Cannas, A., Galetti, D., Girardi, E., Chiacchio, T., Calvo, L., Cuzzi, G., Piacentini, M., Melkonyan, H., Umansky, S. R., Lauria, F. N., Ippolito, G., and Tomei, L. D. (2008) *Mycobacterium tuberculosis* DNA detection in soluble fraction of urine from pulmonary tuberculosis patients. The international journal of tuberculosis and lung disease: the official journal of the International Union against Tuberculosis and Lung Disease 12, 146-151
40. Pierce, K. E., Sanchez, J. A., Rice, J. E., and Wangh, L. J. (2005) Linear-After-The-Exponential (LATE)-PCR: primer design criteria for high yields of specific single-stranded DNA and improved real-time detection. Proc Natl Acad Sci US A 102, 8609-8614
41. Rompler, H., Dear, P. H., Krause, J., Meyer, M., Rohland, N., Schoneberg, T., Spriggs, H., Stiller, M., and Hofreiter, M. (2006) Multiplex amplification of ancient DNA. Nat Protec 1, 720-728
42. Stemmer, W. P. (1994) DNA shuffling by random fragmentation and reassembly: in vitro recombination for molecular evolution. Proc Natl Acad Sci US A 91, 10747-10751
43. Golenberg, E. M., Bickel, A., and Weihs, P. (1996) Effect of highly fragmented DNA on PCR. Nucleic Acids Res 24, 5026-5033
44. Yeku, 0., and Frohman, M. A. (2011) Rapid Amplification of cDNA Ends (RACE). in RNA: Methods and Protocols (Nielsen, H. ed.), Humana Press, Totowa, NJ. pp 107-122
45. Bordelon, H., Ricks, K. M., Pask, M. E., Russ, P. K., Solinas, F., Baglia, M. L., Short, P. A., Nel, A., Blackburn, J., Dheda, K., Zamudio, C., Caceres, T., Wright, D. W., Haselton, F. R., and Pettit, A. C. (2017) Design and use of mouse control DNA for DNA biomarker extraction and PCR detection from urine: Application for transrenal *Mycobacterium tuberculosis* DNA detection. J Microbial Methods 136, 65-70

What is claimed is:

1. A method of amplifying a fragment of a nucleic acid target in a sample comprising:

(a) adding to said sample (i) a nucleic acid template that partially hybridizes to and serves as an amplification template for a fragment of a nucleic acid target, (ii) a U-tolerant DNA polymerase capable of extending the fragment once hybridized to said nucleic acid template, and (iii) a nucleotide tri-phosphate mixture including RNA or DNA uracil bases, wherein adding is under conditions supporting extension of the fragment once hybridized to said acid template;

(b) degrading RNA or DNA uracil bases in the nucleic acid template from the product generated in step (a) and removing or inactivating the U-tolerant DNA polymerase; and (c) contacting the product of step (b) with (i) a U-intolerant polymerase, (ii) a nucleotide triphosphate mixture, and (iii) a forward primer, under conditions supporting polymerization of a nucleic acid strand complementary to the extended fragment, wherein the nucleic acid template comprises a detection sequence and a capture sequence, wherein the detection sequence is located at the 5' end of the nucleic acid template, and wherein the first primer corresponds to a portion of the detection sequence.

2. The method of claim 1, wherein the nucleic acid template comprises a detection sequence and a capture sequence, wherein said detection sequence is 5' to said capture sequence.

3. The method of claim 1, wherein the tolerant DNA polymerase is a heat sensitive polymerase and is heat inactivated after step (a).

4. The method of claim 1, wherein the U-tolerant DNA polymerase is removed after step (a).

5. The method of claim 1, wherein the sample has been treated prior step (a) to increase the concentration of the fragment.

6. The method of claim 1, wherein the sample has been treated after step (a) to increase the concentration of the extended fragment and/or to remove the nucleic acid template.

7. The method of claim 5, wherein the nucleic acid template is coupled to a lipid moiety or a bead.

8. The method of claim 7, further comprising removing the bead coupled nucleic acid template from the preparation of step (a), thereby leaving the extended fragment in solution.

9. The method of claim 8, wherein the bead is a magnetic bead and removing comprises capturing the magnetic bead on a magnetized substrate.

10. The method of claim 1, further comprising degrading any remaining nucleic acid template.

11. The method of claim 1, wherein said nucleic acid template is about 15 to about 2500 nucleotides in length.

12. The method of claim 1, wherein said fragment of nucleic acid target is a deoxyribonucleic acid (DNA) and the first polymerase is a DNA polymerase.

13. The method of claim 12, wherein the fragment of nucleic acid target is from *Mycobacterium tuberculosis*.

14. The method of claim 1, wherein said fragment is a ribonucleic acid (RNA) and the first polymerase is an RNA polymerase.

15. The method of claim 1, further comprising adding a reverse primer after step (b), the reverse primer being:

complementary to the extended fragment and located 3' to the region corresponding to the forward primer; and present at a sufficiently low concentration to effect only linear amplification by polymerase chain reaction of the extended fragment.

16. The method of claim 15, further comprising adding additional reverse primer, thereby resulting in exponential amplification by polymerase chain reaction and subsequent detection of the extended fragment.

17. The method of claim 15, further comprising hybridizing the amplified extended fragment to a probe corresponding to or complementary to the detection sequence.

18. The method of claim 1, wherein the sample is urine.

* * * * *